(12) United States Patent
Elisseeff et al.

(10) Patent No.: US 7,897,165 B2
(45) Date of Patent: *Mar. 1, 2011

(54) METHOD AND MATERIAL FOR ENHANCED TISSUE-BIOMATERIAL INTEGRATION

(75) Inventors: Jennifer Elisseeff, Baltimore, MD (US); Dong-an Wang, Baltimore, MD (US); Anthony Ratcliffe, Del Mar, CA (US)

(73) Assignee: Synthasome, Inc., San Diego, CA (US)

( * ) Notice: Subject to any disclaimer, the term of this patent is extended or adjusted under 35 U.S.C. 154(b) by 759 days.

This patent is subject to a terminal disclaimer.

(21) Appl. No.: 11/369,578

(22) Filed: Mar. 7, 2006

(65) Prior Publication Data

US 2007/0048291 A1   Mar. 1, 2007

Related U.S. Application Data

(63) Continuation of application No. 10/681,752, filed on Oct. 9, 2003, and a continuation-in-part of application No. 11/314,659, filed on Dec. 20, 2005, now abandoned, which is a continuation of application No. 11/090,362, filed on Mar. 25, 2005, now abandoned, which is a continuation of application No. PCT/US2003/030432, filed on Sep. 25, 2003.

(60) Provisional application No. 60/413,152, filed on Sep. 25, 2002, provisional application No. 60/416,881, filed on Oct. 9, 2002.

(51) Int. Cl.
*A61K 31/715* (2006.01)
*A61K 38/39* (2006.01)

(52) U.S. Cl. .................. 424/423; 424/488
(58) Field of Classification Search .......... None
See application file for complete search history.

(56) References Cited

U.S. PATENT DOCUMENTS

| | | | |
|---|---|---|---|
| 5,017,229 A | 5/1991 | Burns et al. | |
| 5,344,459 A | 9/1994 | Swartz | |
| 5,399,665 A | 3/1995 | Barrera et al. | |
| 5,410,016 A | 4/1995 | Hubbell et al. | |
| 5,567,435 A | 10/1996 | Hubbell et al. | |
| 5,573,934 A | 11/1996 | Hubbell et al. | |
| 5,681,353 A | 10/1997 | Li et al. | |
| 5,700,848 A | 12/1997 | Soon-Shiong et al. | |
| 5,709,854 A | 1/1998 | Griffith-Cima et al. | |
| 5,749,968 A | 5/1998 | Melanson et al. | |
| 5,811,094 A | 9/1998 | Caplan et al. | |
| 5,834,274 A | 11/1998 | Hubbell et al. | |
| 5,837,747 A | 11/1998 | Soon-Shiong et al. | |
| 5,858,746 A | 1/1999 | Hubbell et al. | |
| 5,986,043 A | 11/1999 | Hubbell et al. | |
| 6,060,582 A | 5/2000 | Hubbell et al. | |
| 6,123,727 A | 9/2000 | Vacanti et al. | |
| 6,129,761 A | 10/2000 | Hubbell | |
| 6,132,468 A | 10/2000 | Mansmann | |
| 6,224,893 B1 | 5/2001 | Langer et al. | |
| 6,258,870 B1 | 7/2001 | Hubbell et al. | |
| 6,376,742 B1 | 4/2002 | Zdrahala et al. | |
| 6,410,044 B1 | 6/2002 | Chudzik et al. | |
| 6,458,889 B1 | 10/2002 | Trollsas et al. | |
| 6,465,001 B1 | 10/2002 | Hubbell et al. | |
| 6,468,520 B1 | 10/2002 | Rowe et al. | |
| 6,471,993 B1 | 10/2002 | Shastri et al. | |
| 6,554,867 B1 | 4/2003 | Joos | |
| 6,602,294 B1 | 8/2003 | Sittinger et al. | |
| 6,602,975 B2 | 8/2003 | Hubbell et al. | |
| 6,624,245 B2 * | 9/2003 | Wallace et al. | 525/54.1 |
| 6,629,997 B2 | 10/2003 | Mansmann | |
| 6,632,246 B1 | 10/2003 | Simon et al. | |
| 6,632,446 B1 | 10/2003 | Hubbell et al. | |
| 6,639,014 B2 | 10/2003 | Pathak et al. | |
| 6,699,471 B2 | 3/2004 | Radice et al. | |
| 6,712,822 B2 | 3/2004 | Re et al. | |
| 6,713,085 B2 | 3/2004 | Geistlich et al. | |
| 6,723,709 B1 | 4/2004 | Pressato et al. | |

FOREIGN PATENT DOCUMENTS

| | | |
|---|---|---|
| WO | 93/17669 | 9/1993 |
| WO | 94/25080 | 11/1994 |
| WO | WO 02/36147 A1 * | 5/2002 |

OTHER PUBLICATIONS

Hai et al., Bioconjugate Chem., 2000, vol. 11, pp. 705-713.
Benson, Roberto, Nuclear Instruments and Methods in Physics Research B 191, 2002, pp. 752-757.
Aydelotte, M. et al., "Differences between sub-populations of cultured bovine articular chondrocytes. I: Morphology and cartilage matrix production" Connective Tissue Res., vol. 18, pp. 205-222 (1998).

(Continued)

*Primary Examiner*—Jon P Weber
*Assistant Examiner*—Laura Schuberg
(74) *Attorney, Agent, or Firm*—Bose McKinney & Evans LLP

(57) ABSTRACT

The present invention relates to the covalent binding of a hydrogel to an extracellular matrix (ECM). The integration of the hydrogel with the tissue is superior to that in previous techniques. Moreover, unlike previous techniques, the present invention does not require a photoinitiator. Potential therapeutic applications include tissue repair and delivery of drugs or cells.

The ECM is first exposed, then treated with a priming agent. Then a polymerizable agent is added and crosslinked to the ECM.

Two primary embodiments of methods are disclosed. In the first, the priming agent is an oxidizer which creates tyrosyl radicals in the ECM, which are then bound by acrylate groups in the polymerizable agent. In the second, the priming agent contains aldehydes which bind amino groups in the ECM.

28 Claims, 15 Drawing Sheets

OTHER PUBLICATIONS

Aydelotte, M. et al., "Differences between sub-populations of cultured bovine articular chondrocytes. II: Proteoglycan metabolism" Connective Tissue Res., vol. 18, pp. 223-234(1998).

Buckwalter, J. et al., "Articular Cartilage Part I: Tissue Design and chrondrocyte-matrix interactions" The Journal of Bone and Joint Surgery, vol. 79-A, pp. 600-611 (1997).

Buckwalter, J. et al., "Articular Cartilage Part II: Degeneration and osteoarthritis, repair, regeneration, and transplantation" The Journal of Bone and Joint Surgery, vol. 79-A, pp. 612-632 (1997).

Elisseeff, J. et al., "Biological Response of chondrocytes to hydrogels" Ann. N.Y. Acad. Sci. vol. 961, pp. 118-122 (2002).

Elisseeff, J. et al., "Photoencapsulation of chondrocytes in poly(ethylene oxide)-based semi-interpenetrating networks" J. Biomed. Master. res., vol. 51, pp. 164-171 (2000).

Elisseeff, J. et al., "Trasndermal photopolymerization for minimally invasive implatation" Proc. Nat'l. Acad. Sci. USA, vol. 96, pp. 3104-3107(1999).

Healy, K. et al., "Dsigning biomaterials to direct biological responses" Ann. NY Acad. Sci., vol. 875, pp. 24-35 (1999).

Hubbell, J. et al., "Bioactive Biomaterials" Curr. Opin. Biotechnol., vol. 10, pp. 123-129 (1999).

Kim, T.-K, et al., "Experimental Model for Catilage Tissue Engineering to Regernerate the Zonal Organization of Articular Cartilage" OsteoArthritis and Cartilage, vol. 11, pp. 653-664.

Klein, T. et al., "Tissue engineering of stratified articular cartilage from chondrocyte subpopulations" OsteoArthritis and Cartilage, vol. 11, pp. 595-602.

Korver, G. et al., "Compositions of proteoglycans synthesized in different layers of cultured anatomically intact articular cartilage" Matrix, vol. 10, pp. 394-401.

Quinn T. et al., "Controlled enzymatic matrix degradation for integrative cartilage repair" Tissue Engineering, col. 8, pp. 799-806 (2002).

Sawhney, A. et al., "Bioerodibile hydrogels based on photopolymerized poly(ethyleneglycol)-co-poly(alpha-hydroxy acid) diacrylate macromers" Macromolecules, col. 26, pp. 581-587(1993).

Siczkowski, M. et al., "Subpopulations of chondrocytes from different zones of pig articular cartilage" The Journal of Cell Science, vol. 97, pp. 349-360.

Solchaga, L. et al, "Experimental models of cartilage repair: cartilage regeneration using principles of tissue engineering" Clin. Orthopaedics and Related Resolution, vol. 391S, pp. S161-170 (2001).

Temenoff, J. et al., "Review: tissue engineering for regeneration of articular cartilage" Biomaterials, vol. 21, pp. 431-440 (2000).

Waldman, S. et al., "The use of specific choldrocyte populations to modulate the properties of tissue-engineered cartilage" J. Orthopedic Res., col. 14, pp. 424-432.

Wong, M. et al., "Zone-specific cell biosynthetic activity in mature bovine articular cartilage" J. Orthopedic Res., vol. 14, pp. 424-432.

Assam, T. et al., "Cationic polysaccharides for gene delivery" Macromolecules, vol. 35, pp. 9947-9953 (2002).

Y.-R. Chen et al., "An electron spin resonance spin-trapping investigation of the free radicals formed by the reaction of mitochondrial cytochrome c oxidase with H202" J. Biol. Chem., col. 274, pp. 3308-3314 (1999).

S. Qian et al., "Identification of protein-derived tyrosyl radical in the reaction of cytochome c and hydrogen peroxide" Biochem. J., vol. 363, pp. 281-288 (2002).

Q. Li et al., "Heterogeneous-Phase Reaction of Clycidyl Methacrylate and Chondroitin Sulfate: Mechanism of Ring-Opening-Transesterificiation Competition" Macrmolecules, col. 36, pp. 2556-2562 (2003).

Kim, T.-K, et al., "Experimental Model for Catilage Tissue Engineering To Regernerate the Zonal Organization of Articular Cartilage" OsteoArthritis and Cartilage, vol. 11, pp. 653-664, 2003.

Klein, T et al., "Tissue engineering of stratified articular cartilage from chondrocyte subpopulations" OsteoArthritis and Cartilage, vol. 11, pp. 595-602, 2003.

Korver, G. et al., "Compositions of proteoglycans synthesized in different layers of cultured anatomically intact articular cartilage" Matrix, vol. 10, pp. 394-401, 1990.

Siczkowski, M. et al., "Subpopulations of chondrocytes from different zones of pig articular cartilage" The Journal of Cell Science, vol. 97, pp. 349-360, 1990.

Waldman, S. et al., "The use of specific choldrocyte populations to modulate the properties of tissue-engineered cartilage" J. Orthopedic Res., col. 14, pp. 424-432, 2003.

Wong, M. et al., "Zone-specific cell biosynthetic activity in mature bovine articular cartilage" J. Orthopedic Res., vol. 14, pp. 424-432, 1996.

* cited by examiner

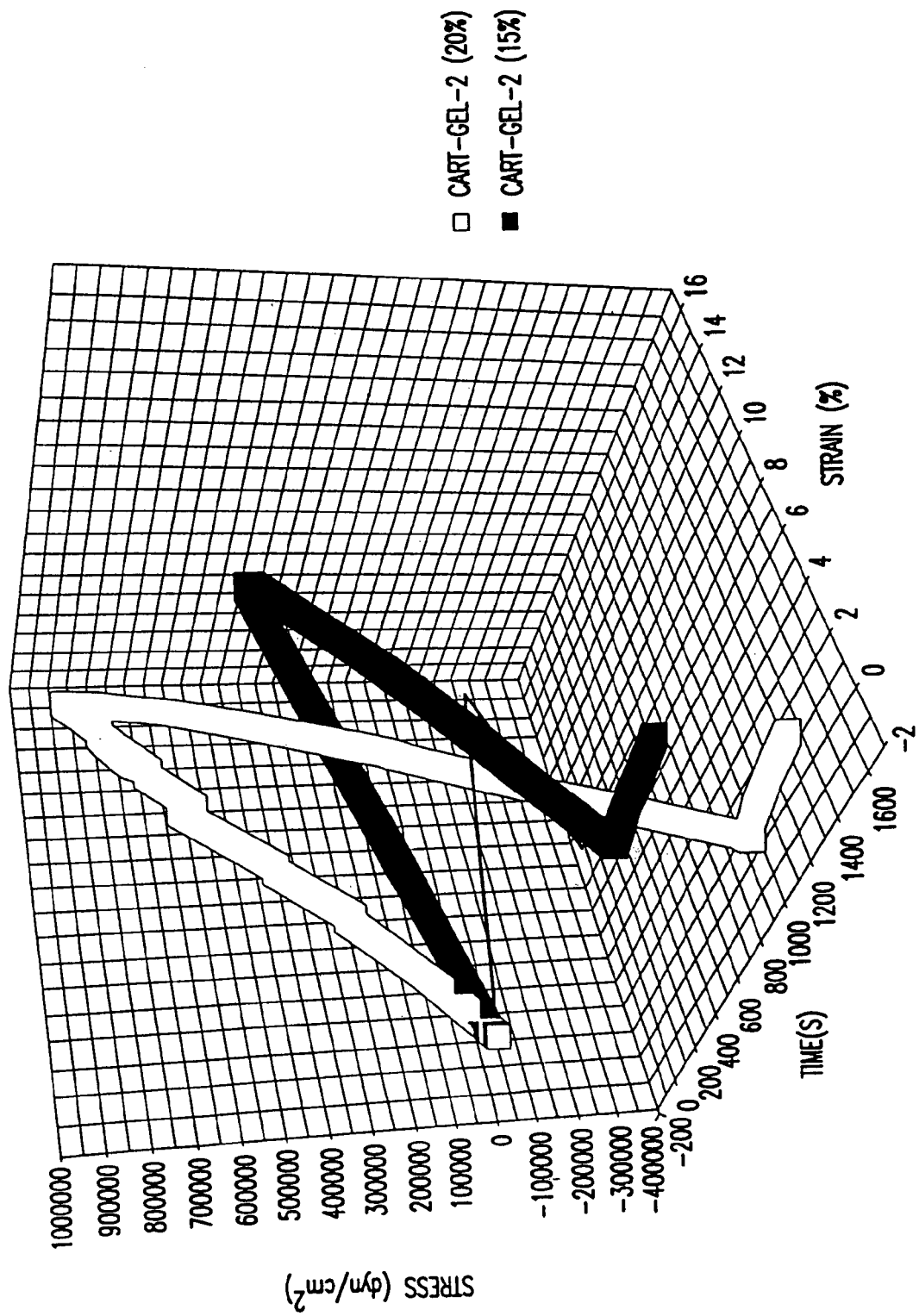

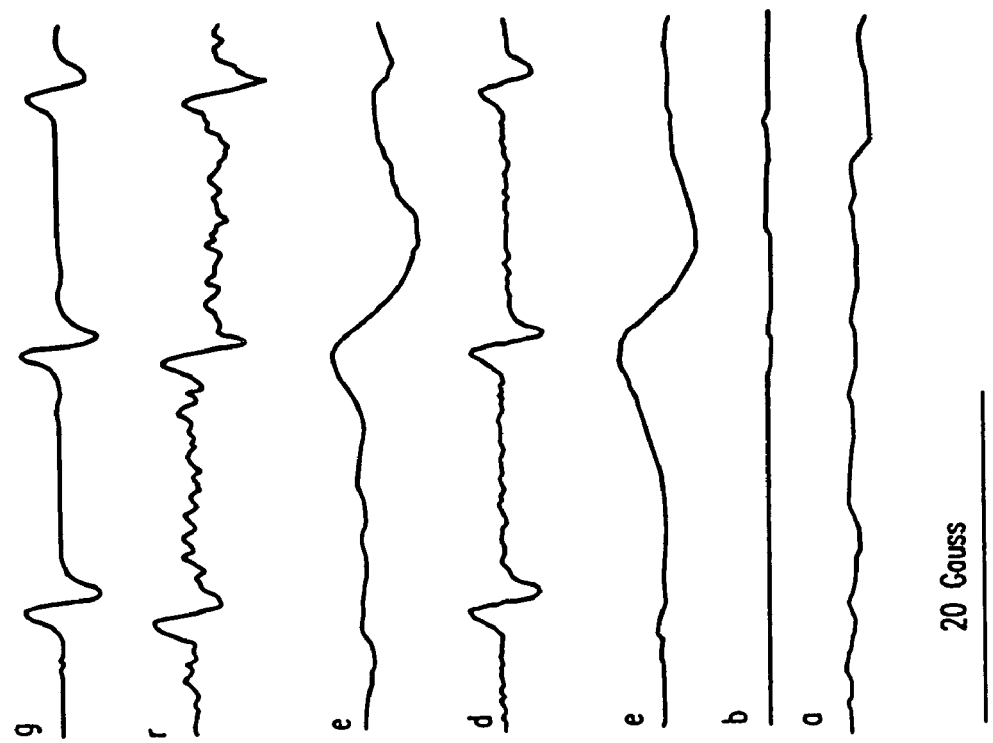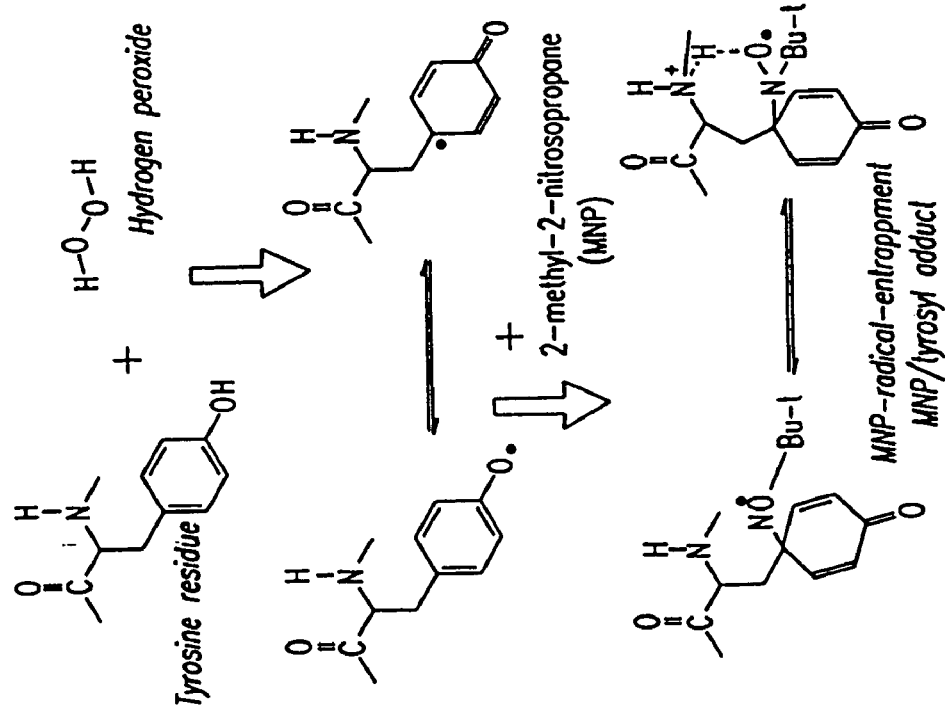
FIG. 5

METHOD AND MATERIAL FOR ENHANCED TISSUE-BIOMATERIAL INTEGRATION

CROSS-REFERENCE TO RELATED APPLICATIONS

This application claims benefit under 35 U.S.C. 119(e) of U.S. Provisional Application No. 60/416,881, filed Oct. 9, 2002, the entire disclosure of which is hereby incorporated by reference.

This application is related to a utility patent application claiming priority to U.S. Provisional Application No. 60/413,152 (filed Sep. 25, 2002), entitled "Cross-linked polymer matrices, and methods of making and using same," and filed on Sep. 25, 2003, the entire disclosure of which is hereby incorporated by reference.

BACKGROUND OF THE INVENTION

1. Field of the Invention

The present invention pertains to a method of creating a hydrogel covalently bound to the extracellular matrix. More specifically, this invention is directed to a polymer hydrogel covalently bound to an extracellular matrix, and to a method for creating such a hydrogel, in a tissue-initiated polymerization.

2. Background Art

Integration of biomaterials with the body is a longstanding problem in medicine. Lack of proper integration with the body sacrifices implant longevity and function. Hard tissues such as cartilage and bone present particular challenges to integration.

Cartilage lacks the ability to repair itself, and has a dense extracellular matrix that provides a smooth surface with weight bearing function, making cartilage extremely challenging to integrate with other materials. Collagen fibers present in the cartilage matrix and throughout the body have structural integrity and are therefore a target for anchoring and biomaterial integration.

Earlier work (e.g. Langer et al., U.S. Pat. No. 6,224,893; Hubbell et al., U.S. Pat. No. 6,258,870; Hubbell et al., U.S. Pat. No. 6,465,001) on biological applications for polymers relied on photoinitiators to capture light energy and form free radicals to initiate polymerization of the polymer precursors. For example, in U.S. Pat. Nos. 6,258,870 and 6,465,001, the use of ethyl eosin is recommended. An advantage of certain embodiments of the present invention, wherein appropriate free radicals are produced following localized mild oxidation of the tissue, is that no photoinitiator is required, saving complexity and expense, and alleviating any issue of toxicity of the photoinitiator.

Most notably, the polymers of the prior art (e.g. Langer et al., U.S. Pat. No. 6,224,893; Hubbell et al., U.S. Pat. No. 6,258,870; Hubbell et al., U.S. Pat. No. 6,465,001) do not bind-covalently to the tissue. This profoundly limits the strength and durability of these inventions, as they do not integrate well as possible with the tissue.

SUMMARY OF THE INVENTION

It is a general object of the invention to create a hydrogel covalently bound to an extracellular matrix.

In a first preferred embodiment of the invention, the method comprises the following steps:
(a) providing an exposed extracellular matrix;
(b) priming the extracellular matrix by treating with a priming agent to create a primed extracellular matrix;
(c) adding to the primed extracellular matrix a solution of a polymerizable agent; and
(d) reacting the primed extracellular matrix and polymerizable agent to create a hydrogel covalently bound to the extracellular matrix.

As used in this description and in the appended claims, "solution" means a solution, a suspension, or a colloid.

In a second preferred embodiment of the invention, the extracellular matrix comprises a plurality of tyrosine residues, the priming step comprises oxidizing the extracellular matrix, the priming agent comprises an oxidizing agent, the primed extracellular matrix comprises a plurality of tyrosyl radicals, the polymerizable agent comprises an acrylate group reactable with the tyrosyl radicals, and the reacting step comprises binding the polymerizable agent to the tyrosyl radicals and crosslinking the polymerizable agent.

In a further preferred embodiment, the extracellular matrix of the second embodiment is in a living body, preferably that of a mammal, or most preferably in a human body.

In yet another preferred embodiment, the extracellular matrix of the second embodiment is exposed by treating with chondroitinase ABC.

In a still further preferred embodiment, the extracellular matrix of the second embodiment comprises a collagen. In a yet further embodiment, the collagen is in a cartilage.

In yet another preferred embodiment, the oxidizing agent of the second embodiment comprises a hydrogen peroxide solution. Alternate oxidizing agents may be used, including vitamin C.

In a still further preferred embodiment, the priming step of the second embodiment further includes exposing said extracellular matrix and said polymerizable agent to a source of electromagnetic radiation. In an even more preferred embodiment, the source of electromagnetic radiation is a source of ultraviolet radiation In yet another preferred embodiment, the polymerizable agent of the second embodiment has at least one free radical polymerizable group selected from the group consisting of an of an acrylate, a diacrylate, oligoacrylate, dimethacrylate, and oligomethacrylate.

In a still further preferred embodiment, the reacting step of the second embodiment comprises exposing said extracellular matrix and said polymerizable agent to a source of ultraviolet radiation.

In yet another preferred embodiment, the crosslinking of the second embodiment is by using a redox initiator. In a still further preferred embodiment, an ionic crosslinking reaction is used. In still another preferred embodiment, an enzymatic crosslinking reaction is used.

In a still further preferred embodiment, the method of the second embodiment is carried out transdermally.

In yet another preferred embodiment, a diffusible drug substance is added with said polymerizable agent of the second embodiment.

In a still further preferred embodiment, a plurality of living cells are added with said polymerizable agent of the second embodiment.

In yet another preferred embodiment, a solid repair in a tissue is created by the second embodiment.

A third preferred embodiment is the hydrogel produced by the method comprising the following steps:
(a) providing an exposed extracellular matrix;
(b) priming the extracellular matrix by treating with a priming agent to create a primed extracellular matrix;
(c) adding to the primed extracellular matrix a solution of a polymerizable agent; and (d) reacting the primed extracellular matrix and polymerizable agent to create a hydrogel covalently bound to the extracellular matrix; wherein said extracellular matrix comprises a plurality of tyrosine residues, said priming step comprises oxidizing said extracellular matrix, said priming agent comprises an oxidizing agent, said primed extracellular matrix comprises a plurality of tyrosyl radicals, said polymerizable agent comprises an acrylate group reactable with said tyrosyl radicals, and said reacting step comprises binding said polymerizable agent to the tyrosyl radicals and crosslinking said polymerizable agent.

A fourth preferred embodiment is a hydrogel covalently bound to an extracellular matrix at a plurality of tyrosine residues of said matrix. Yet another preferred embodiment is the hydrogel of the third embodiment wherein said extracellular matrix is composed of a plurality of collagen fibers in a cartilage matrix.

A fifth preferred embodiment is a method of forming a hydrogel covalently bound to a cartilage tissue, comprising the steps of:
(a) exposing a plurality of tyrosine residues disposed in a plurality of collagen fibers further disposed in a cartilage tissue by treating the tissue with a glycanase to remove a plurality of polysaccharides;
(b) oxidizing the tyrosine residues, by treating with a hydrogen peroxide solution and a source of ultraviolet light, to produce a plurality of tyrosyl groups in the collagen;
(c) adding a polymerizable agent comprising one or more acrylate groups; and
(d) reacting the tyrosyl groups and the polymerizable agent to create a hydrogel covalently bound to the collagen.

In a sixth preferred embodiment, the method is that of the first enumerated embodiment, wherein: the extracellular matrix comprises a plurality of amino groups, the priming agent comprises a compound with an aldehyde group and a carrier compound with an amino group, the priming step comprises reacting the priming agent with the extracellular matrix to covalently bind the extracellular matrix and the priming agent, the primed extracellular matrix consists of the extracellular matrix covalently bound to the priming agent, and the reacting step consists of covalently binding the polymerizable agent to the primed extracellular matrix and crosslinking the polymerizable agent.

In a further preferred embodiment, the extracellular matrix of the sixth embodiment is in a living body, preferably that of a mammal, or most preferably in a human body.

In yet another preferred embodiment, the polymerizable agent of the sixth embodiment has at least one free radical polymerizable group selected from the group consisting of an of an acrylate, a diacrylate, oligoacrylate, dimethacrylate, and oligomethacrylate.

In a still further preferred embodiment, the reacting step of the sixth embodiment comprises exposing said extracellular matrix and said polymerizable agent to a source of ultraviolet radiation.

In yet another preferred embodiment, the crosslinking of the sixth embodiment is by using a redox initiator. In a still further preferred embodiment, an ionic crosslinking reaction is used. In still another preferred embodiment, an enzymatic crosslinking reaction is used.

In a still further preferred embodiment, the method of the sixth embodiment is carried out transdermally.

In yet another preferred embodiment, a diffusible drug substance is added with said polymerizable agent of the sixth embodiment.

In a still further preferred embodiment, a plurality of living cells are added with said polymerizable agent of the sixth embodiment.

In yet another preferred embodiment, a solid repair in a tissue is created by the sixth embodiment.

A seventh preferred embodiment is the hydrogel produced by the method comprising the steps of:
(a) providing an exposed extracellular matrix;
(b) priming the extracellular matrix by treating with a priming agent to create a primed extracellular matrix;
(c) adding to the primed extracellular matrix a solution of a polymerizable agent; and
(d) reacting the primed extracellular matrix and polymerizable agent to create a hydrogel covalently bound to the extracellular matrix; wherein, said extracellular matrix comprises a plurality of amino groups, said priming agent comprises a compound with an aldehyde group and a carrier compound with an amino group, said priming step comprises reacting said priming agent with said extracellular matrix to covalently bind said extracellular matrix and said priming agent, said primed extracellular matrix consists of said extracellular matrix covalently bound to said priming agent, and said reacting step consists of covalently binding said polymerizable agent to said primed extracellular matrix and crosslinking said polymerizable agent.

An eighth preferred embodiment is a hydrogel covalently bound via a priming agent to an extracellular matrix at a plurality of amino groups in said extracellular matrix.

BRIEF DESCRIPTION OF THE DRAWINGS

FIGS. 3 E-H represent the rheological behavior.

FIG. 5 shows analysis of the acrylate-tyrosyl reaction mechanism using electron spin-trapping.

DETAILED DESCRIPTION OF THE INVENTION

Figure 1:
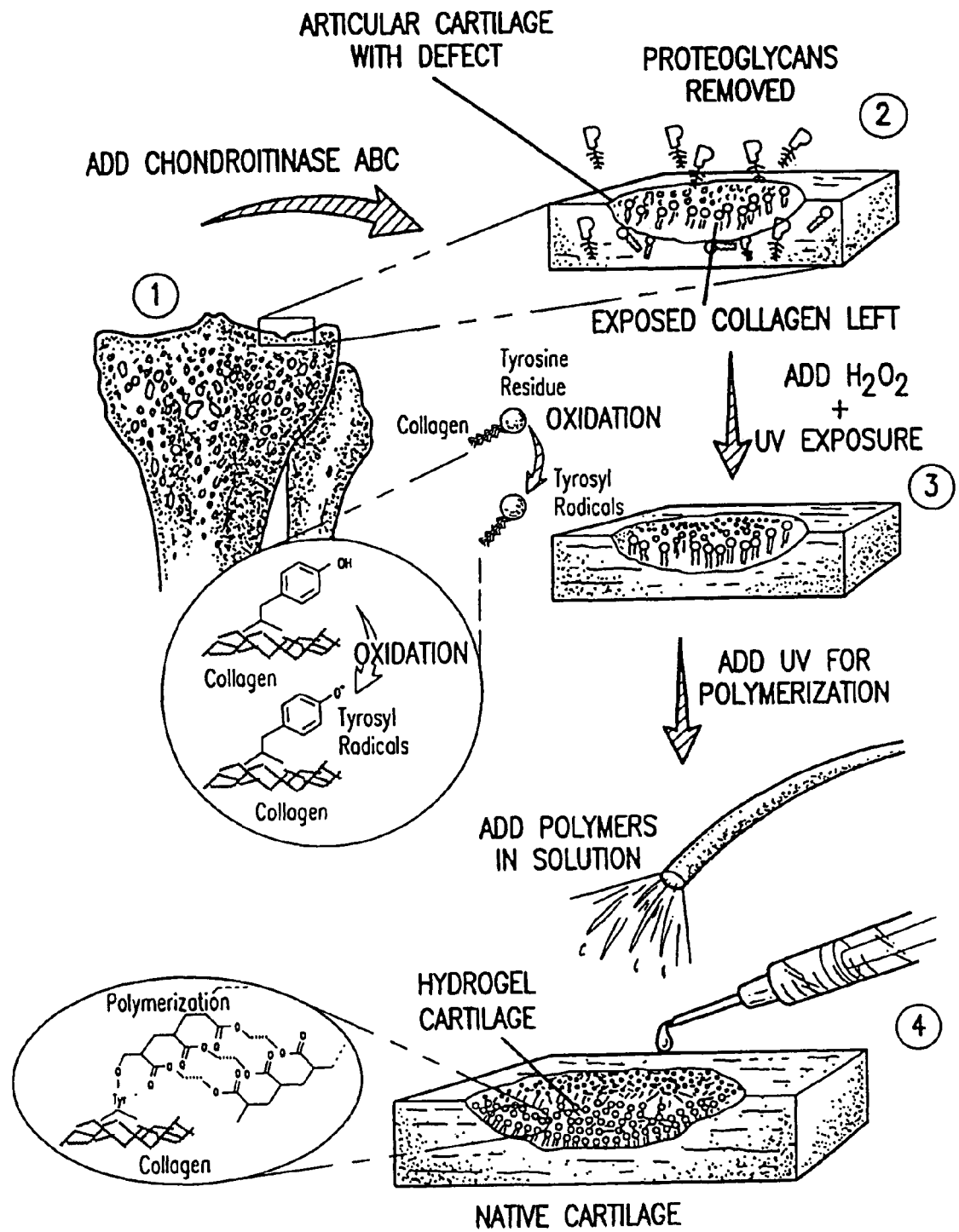
FIG. 1 is a schematic description of the method as applied to cartilage using acrylate-tyrosyl chemistry.

Biomaterials play an important role in medicine today with applications ranging from medical devices to artificial implants, drug delivery coatings, and scaffolds for tissue regeneration. The strategy for biomaterial design has evolved from the philosophy of creating materials that were "invisible" to the body, to the development of biomaterials that actively interact with the surrounding tissue by recruiting cells, stimulating regeneration, or guiding tissue remodeling.

Thus, the body is encouraged to positively integrate with a biomaterial instead of "walling off" the implant with a fibrous capsule to silence reactions. The interface between a biomaterial and surrounding tissue is integral to its functionality and long-term performance, particularly in musculoskeletal implants. Integration of biomaterials with hard tissues such as cartilage and bone is particularly challenging due to the nature of the dense extracellular matrix and strong mechanical forces that the tissue must withstand. Furthermore, cartilage tissue lacks the ability to heal and has difficulty integrating with natural or engineered cartilage, much less a biomaterial, and was therefore chosen as our model system.

Heretofore, true integration of biomaterials by covalent binding of the materials to an extracellular matrix has not been achieved.

The present invention relates to covalent attachment of biogels to the extracellular matrix. Principles of basic protein biochemistry are combined with biomaterials to create a general system for directed integration of biomaterials that may be applied to multiple tissues types and biomaterial applications.

The term "hydrogel" as used herein and in the appended claims refers to a hydrophilic cross-linked polymer capable of containing a large volume fraction of water. More preferably hydrogels according to the present invention can contain greater than about 70-90 volume % water. When a hydrophilic polymer is formed in situ, it may inherently acquire water from its environment or from solutions used to create the hydrogel.

The term "cross-linked" as used herein and in the appended claims refers to a composition containing intermolecular cross-links and optionally intramolecular cross-links arising from the formation of covalent bonds, ionic bonds, hydrogen bonding, or any combination thereof. "Cross-linkable" refers to a component or compound that is capable of undergoing reaction to form a cross-linked composition.

The polymerizable agent of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The polymerizable agent should be substantially hydrophilic and biocompatible.

The term "biocompatible" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 mL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers, polymer matrices, and formulations of the present invention may also be evaluated by well-known in vivo tests, such as subcutaneous implantations in rats to confirm that they do not cause significant levels of irritation or inflammation at the subcutaneous implantation sites.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly (propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Examples of materials which can be used to form a hydrogel include modified alginates. Alginate is a carbohydrate polymer isolated from seaweed, which can be crosslinked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel, which are derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., *Obstetrics & Gynecology*, vol. 77, pp. 48-52 (1991); and Steinleitner et al., *Fertility and Sterility*, vol. 57, pp. 305-308 (1992). Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically crosslinkable groups. Methods for modifying hydrophilic polymers to include these groups are well known to those of skill in the art.

The polymers may be intrinsically biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 daltons or below. Usable, but less preferable for general use because of intrinsic biodegradability, are water-soluble natural polymers and synthetic equivalents or derivatives, including polypeptides, polynucleotides, and degradable polysaccharides.

The polymers can be a single block with a molecular weight of at least 600, preferably 2000 or more, and more preferably at least 3000. Alternatively, the polymers can include can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Covalently Crosslinkable Polymer Solutions

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., *ASAIO Trans.*, vol. 38, pp. 154-157 (1992).

The term "active species polymerizable group" is defined as a reactive-functional group that has the capacity to form additional covalent bonds resulting in polymer interlinking upon exposure to active species. Active species include free radicals, cations, and anions. Suitable free radical polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In one embodiment, the active species polymerizable groups are preferably located at one or more ends of the hydrophilic polymer. In another embodiment, the active species polymerizable groups are located within a block copolymer with one or more hydrophilic polymers forming the individual blocks. The preferred polymerizable groups are acrylates, diacrylates, oligoacrylates, dimethacrylates, oligomethacrylates, and other biologically acceptable photopolymerizable groups. Acrylates are the most preferred active species polymerizable group.

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

Naturally occurring and synthetic polymers may be modified using chemical reactions available in the art and described, for example, in March, "Advanced Organic Chemistry," 4th Edition, 1992, Wiley-Interscience Publication, New York. Such methods may be used to, for example, introduce acrylate groups as described herein.

Preferably, the hydrophilic polymers that include active species or crosslinkable groups include at least 1.02 polymerizable or crosslinkable groups on average, and, more preferably, each includes two or more polymerizable or crosslinkable groups on average. Because each polymerizable group will polymerize into a chain, crosslinked hydrogels can be produced using only slightly more than one reactive group per polymer (i.e., about 1.02 polymerizable groups on average). However, higher percentages are preferable, and excellent gels can be obtained in polymer mixtures in which most or all of the molecules have two or more reactive double bonds. Poloxamines, an example of a hydrophilic polymer, have four arms and thus may readily be modified to include four polymerizable groups.

Source of Cells

The hydrogel can be used for delivery of cells. Cells can be obtained directed from a donor, from cell culture of cells from a donor, or from established cell culture lines. In the preferred embodiment, cells of the same species and preferably same immunological profile are obtained by biopsy, either from the patient or a close relative, which are then grown to confluence in culture using standard conditions and used as needed. If cells that are likely to elicit an immune reaction are used, such as human muscle cells from immunologically distinct individual, then the recipient can be immunosuppressed as needed, for example, using a schedule of steroids and other immunosuppressant drugs such as cyclosporine. However, in the most preferred embodiment, the cells are autologous. Cells may also be obtained from the blood of the patient, for example by apheresis.

In the preferred embodiments, cells are obtained directly from a donor, washed and implanted directly in combination with the polymeric material. The cells are cultured using techniques known to those skilled in the art of tissue culture. Cells obtained by biopsy are harvested and cultured, passaging as necessary to remove contaminating cells. Isolation of chondrocytes and muscle cells is demonstrated in WO 94/25080, the disclosure of which is incorporated herein.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production.

Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labelled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

Biologically Active Materials Added

The hydrogel can be used for drug delivery. Examples of materials to be incorporated into hydrogels are proteins, polysaccharides, nucleic acid molecules, and synthetic organic or inorganic molecules. These may be useful for therapeutic, prophylactic or diagnostic purposes. Drugs may include antibiotics, antivirals, chemotherapeutic agents, anti-angiogenic agents, hormones, drugs having an effect on vascular flow, anti-inflammatories, and many others routinely used.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-polymer suspension prior to formation of implant or transplantation. Alternatively, the hydrogel could be modified to bind humoral factors or signal recognition sequences prior to combination with isolated cell suspension.

Blends of Ionically and Covalently Crosslinkable Polymers

In a preferred embodiment, the polymer solution is formed of two or more polymers, which crosslink to form a semi-interpenetrating network. For example, the blend could include PEO, which is ionically crosslinkable, and diamethacrylated PEO, in a range of between 10 and 40% by weight covalently crosslinkable polymer in the preferred embodiment. Alternatively, blends of two covalently crosslinkable polymers can be used, selected on the basis that they form a network of crosslinked homopolymers, not to each other. Advantages of the semi-interpenetrating networks include that the diffusion of non-crosslinked polymer can provide advantages degradation properties, and enhance mechanical properties, especially for use in plastic surgery.

Cell Suspensions

Preferably the polymer is dissolved in an aqueous solution, preferably a 0.1 M potassium phosphate solution, at physiological pH, to a concentration forming a polymeric hydrogel. The isolated cells are suspended in the solution to a concentration of between 1 and 50 million cells/ml, most preferably between 10 and 20 million cells/ml.

Methods of Implantation

In a preferred embodiment, the molecules or cells to be delivered are mixed with the polymerizable agent and injected directly into a site where it is desired to implant the molecules or cells, prior to crosslinking of the polymer to form the hydrogel.

The site, or sites, where molecules or cells are to be injected is determined based on individual need, as is the requisite amount of molecules or number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma or burns. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscope or thoracoscope to any intraperitoneal or extraperitoneal or thoracic organ. For example, the suspension could be injected in the region of the gastroesophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

The material can also be used to treat vesicoureteral reflux. In addition to its use for the endoscopic treatment of reflux, the system of injectable autologous muscle cell may also be applicable for the treatment of other medical conditions, such as urinary and rectal incontinence, dysphonia, plastic reconstruction, and wherever an injectable permanent biocompatible material is needed. Methods for using an injectable polymer for delivering isolated cells via injection are described for example in WO 94/25080.

In addition to the use of the cell-polymer suspension for the treatment of reflux and incontinence, the suspension can also be applied to reconstructive surgery, as well as its application anywhere in the human body where a biocompatible permanent injectable material is necessary. The suspension can be injected endoscopically, for example through a laryngoscope for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

This technology can be used for other purposes. For example, custom-molded cell implants can be used to reconstruct three dimensional tissue defects, e.g., molds of human ears could be created and a chondrocyte-hydrogel replica could be fashioned and implanted to reconstruct a missing ear. Cells can also be transplanted in the form of a three-dimensional structure which could be delivered via injection.

The present invention will now be described with reference to certain instructive, non-limiting examples.

EXAMPLES AND TESTING OF TYROSYL-MEDIATED INTEGRATION

The present embodiment relates to tissue-initiated photopolymerization wherein the tissue actively causes light-induced gelation or photopolymerization and true tissue-biomaterial integration occurs.

An exemplary method according to the present invention for covalently bonding a polymer to an extracellular matrix is discussed below. Specifically a method for covalently attaching a polymer to cartilage or "tissue-initiated photopolymerization" using acrylate-tyrosyl chemistry is depicted in FIG. 1. The method comprises the steps of (1) removing polysaccharides in cartilage to expose the collagen network by enzyme treatment; (2) in situ generation of tyrosyl radicals by photo-oxidation of tyrosine residues on collagen with $H_2O_2$ under low intensity UV irradiation, thereby priming the extracellular matrix; and (3) introduction of a macromer solution of a polymerizable agent and in situ photo-gelation via tyrosyl radical initiation and UV-excitation. Since the reaction is initiated by components of the tissue, the macromers are grafted (covalently react) with the tissue in addition to crosslinking (gelation) to form a solid, crosslinked network. If enzymatic treatment or oxidative treatment were performed alone, no hydrogel was formed when the macromer and cartilage were exposed to light. However, in some environments the tissue will be minimally glycosylated, so incorporation may proceed in some instances without necessity of enzymatic treatment.

Collagen is a ubiquitous protein in the body, serving both structural and biological roles, and is thus an ideal target for biomaterial integration according to the present invention. Crosslinked Type II collagen in cartilage is responsible for the impressive tensile and dynamic mechanical properties of the tissue, making it an ideal target to initiate and anchor a polymer implant. However, collagen is not the only suitable extracellular matrix protein for the methods of the present invention: any protein with significant numbers of exposable tyrosine residues will be suitable.

Example I

An exemplary in vitro protocol is discussed below. Surfaces of fresh fetal bovine cartilage chips were treated with chondroitinase ABC (5 unit/ml, in Tris pH 8.1) at 37° C. for 1 hr. Photo-oxidation of these surfaces was performed for 5 min with $H_2O_2$ (5%) and UV-irradiation (365 nm; 3 mW/cm$^2$). Excess $H_2O_2$ was removed. Pre-argon-bubbled PEODM (poly[ethylene glycol]dimethacrylate, 15% and 20%, w/v) were added to the cartilage surfaces without photo-initiators. The reactants underwent the UV-irradiation (365 nm; 8 mW/cm$^2$) for 30 min.

Figure 2:
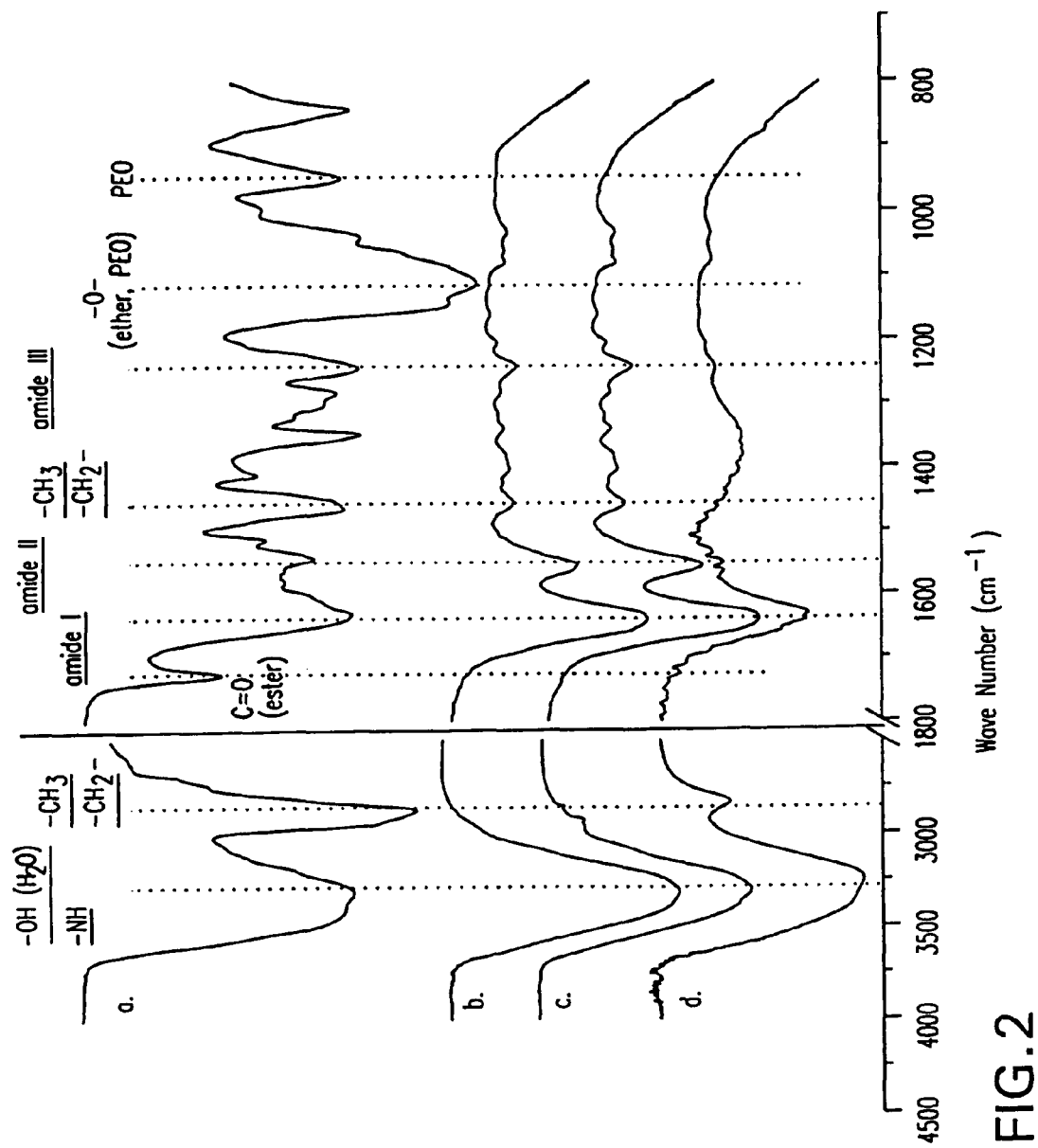
FIG. 2 is a series of spectrograms of treated cartilage at various stages of the procedure using attenuated total reflectance Fourier transform infrared spectroscopy (ATR-FTIR).
Figure 3A:
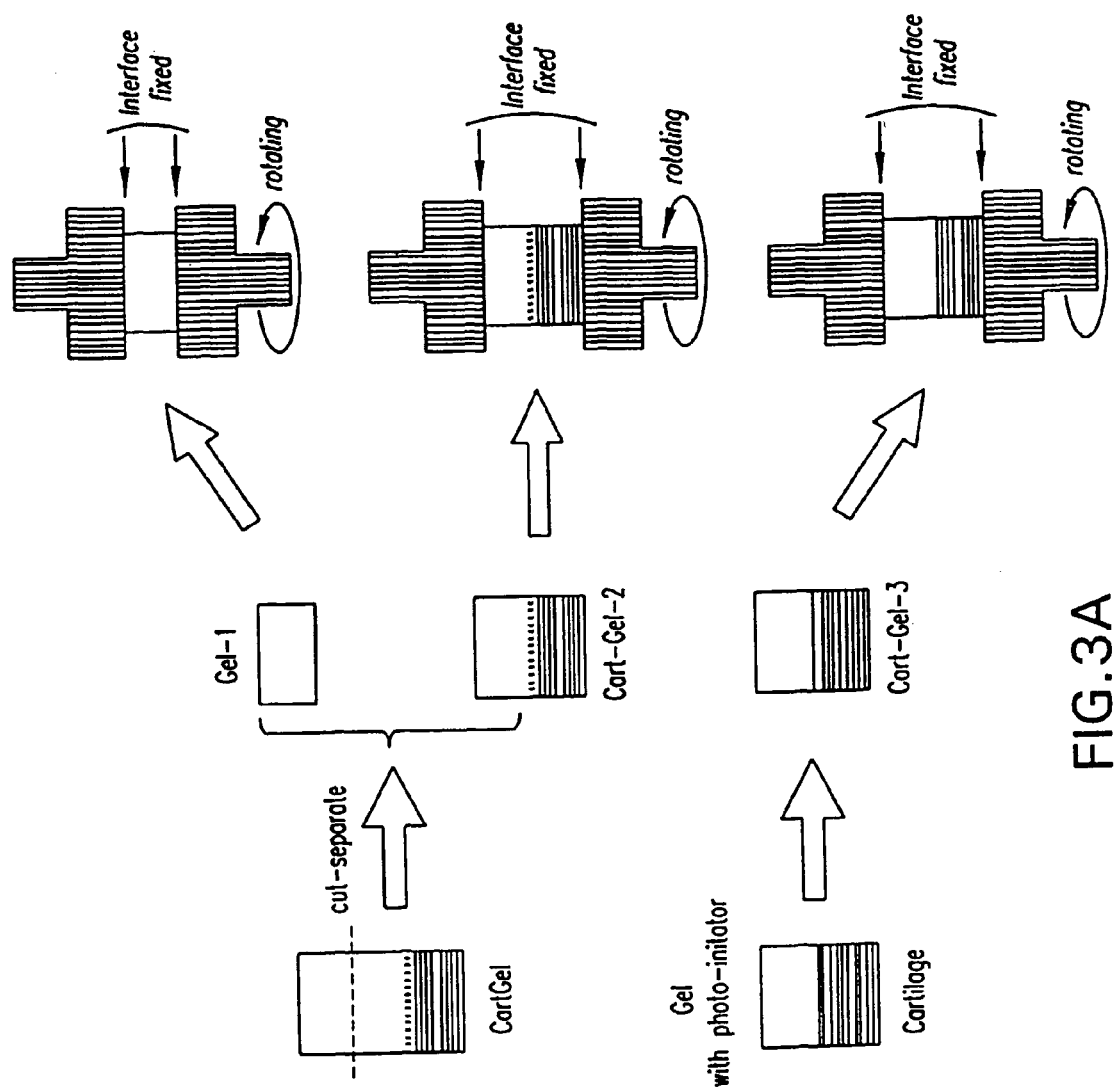
FIG. 3A is a schematic of the testing procedure.
Figure 3B:
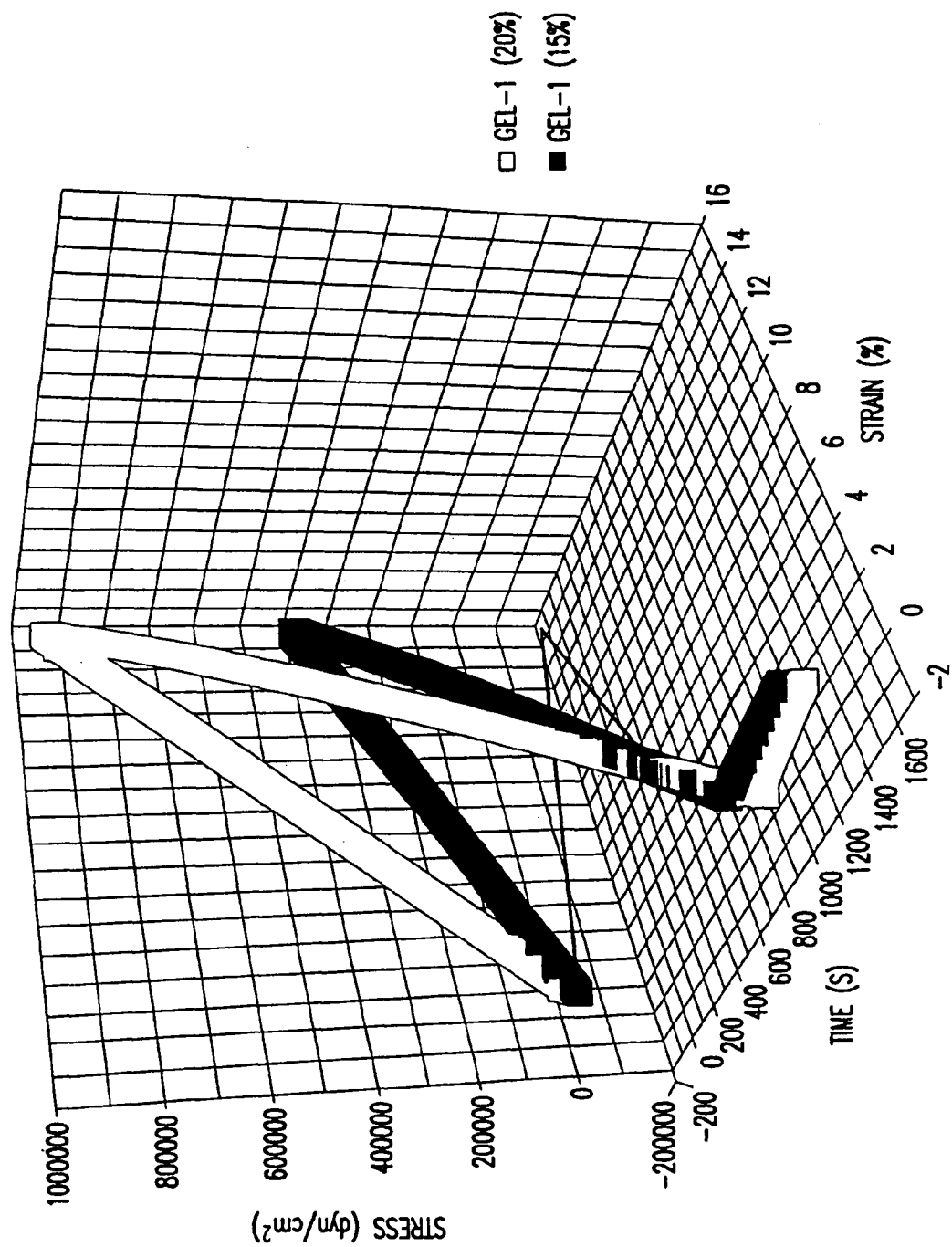
FIGS. 3B-D represent the stress-strain-time behavior.
Figure 3D:
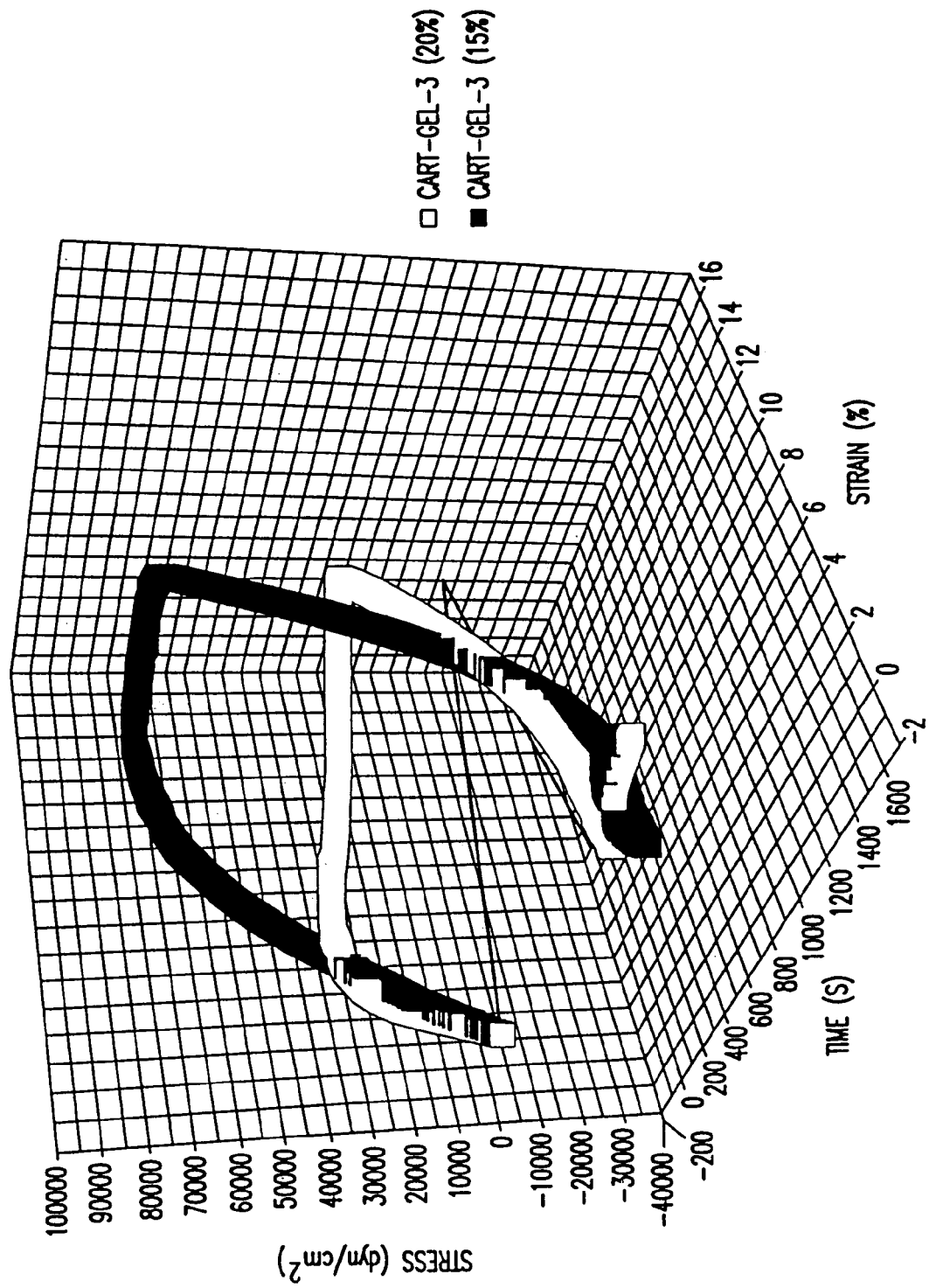
Figure 3E:
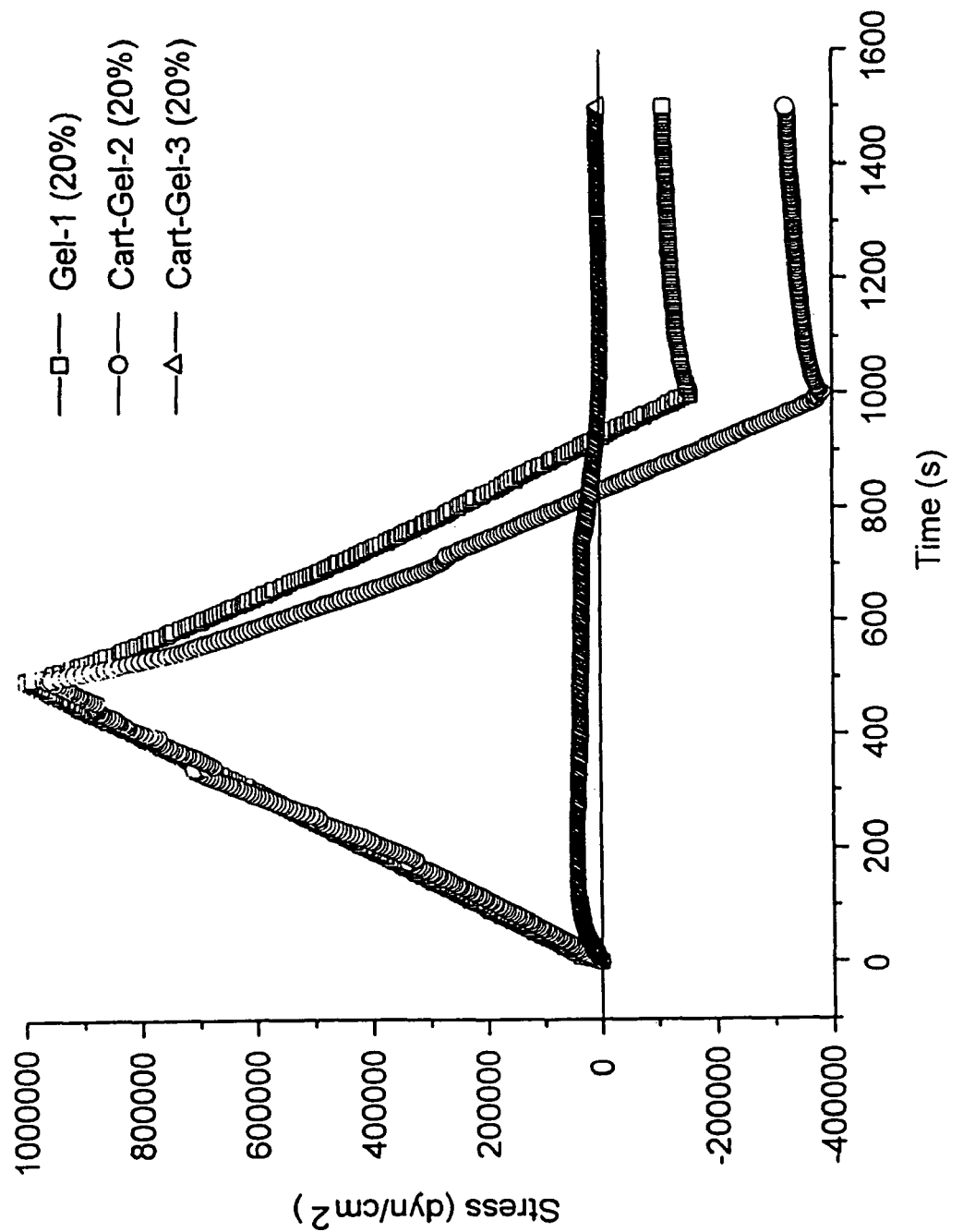
FIG. 3 shows the results of tests of the mechanical functionality of hydrogel alone, and of two hydrogels on a cartilage surface.
FIG. 3I indicates the applied strain-time conditions.
Figure 3F:
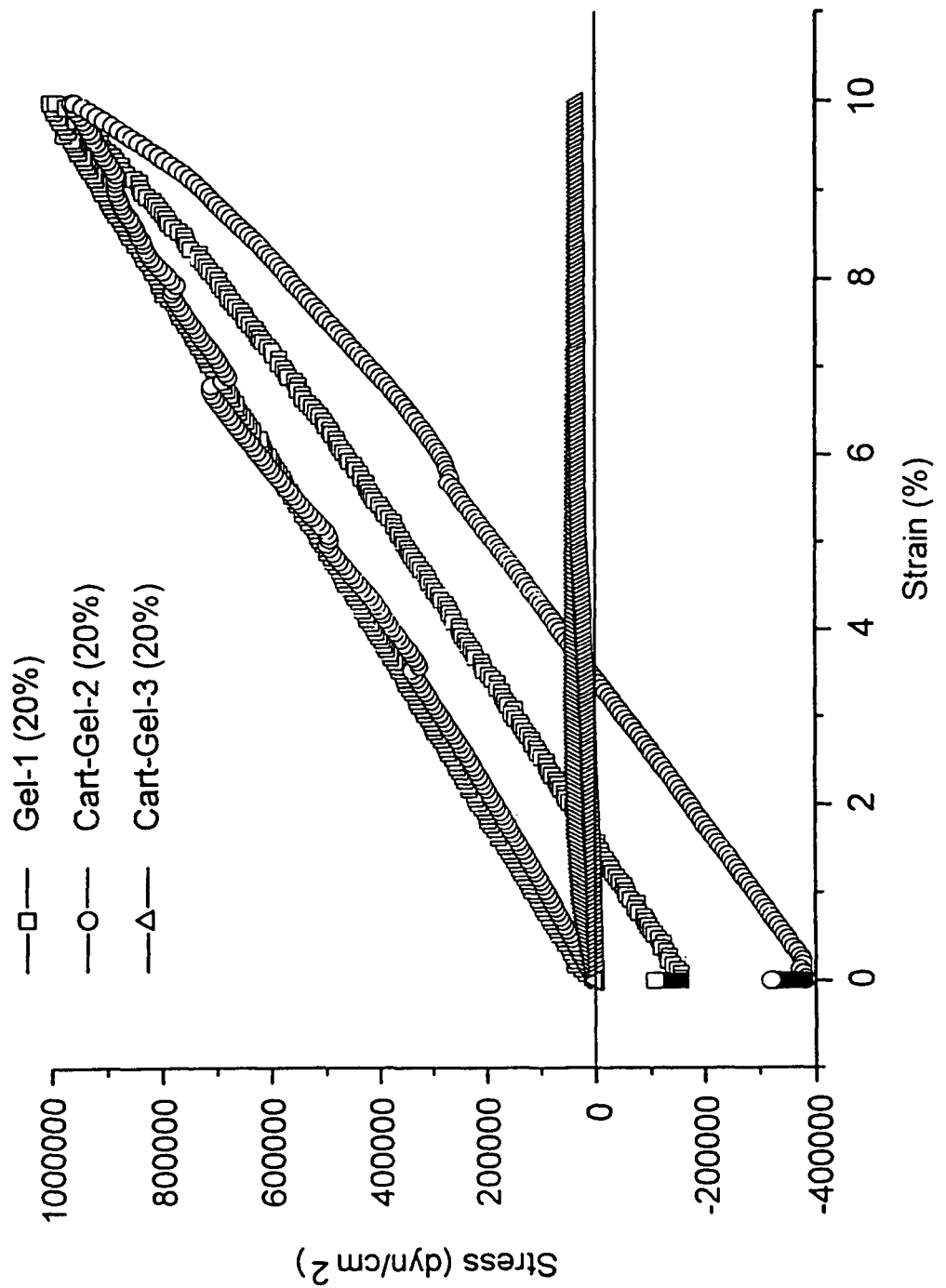
Figure 3G:
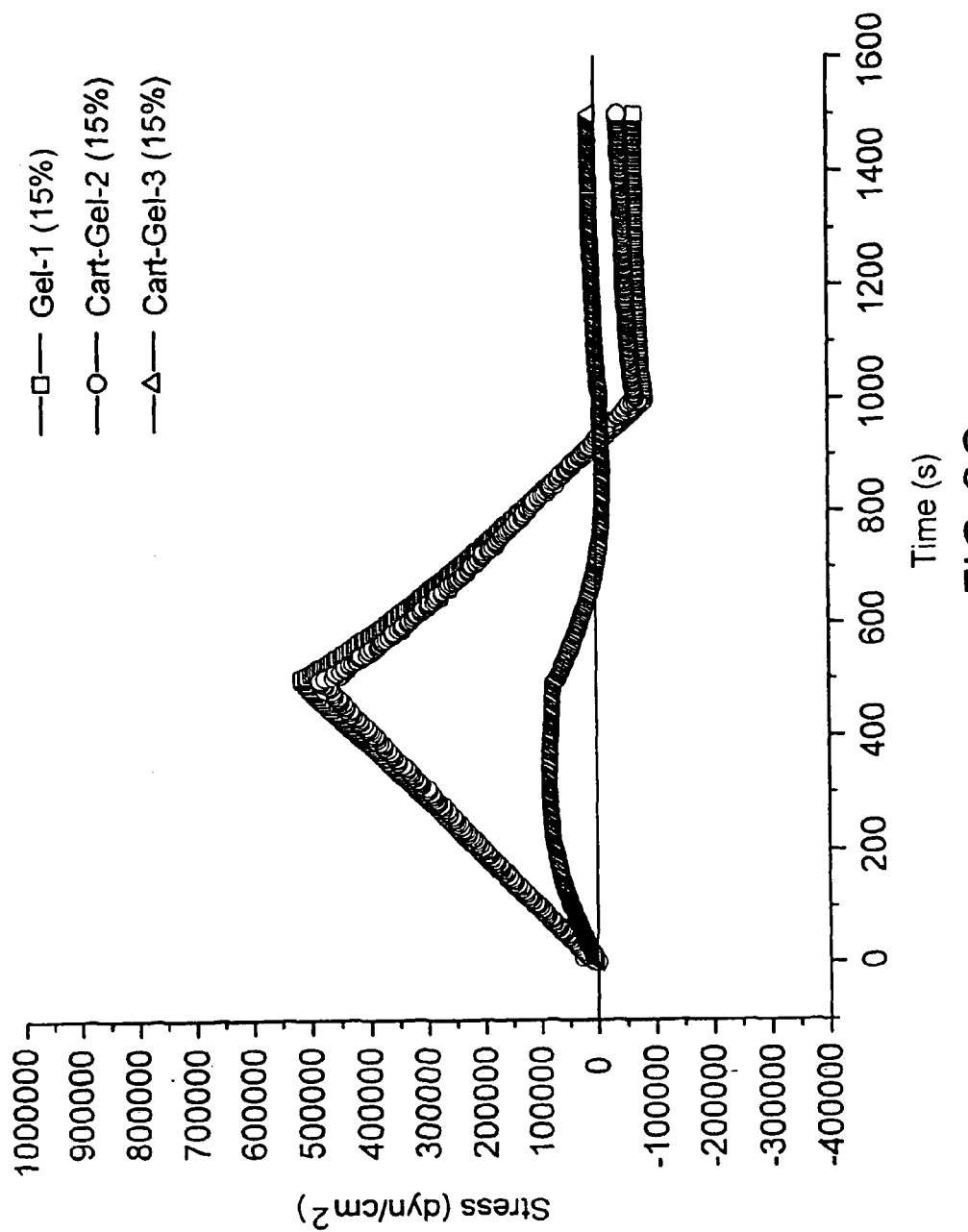
Figure 3H:
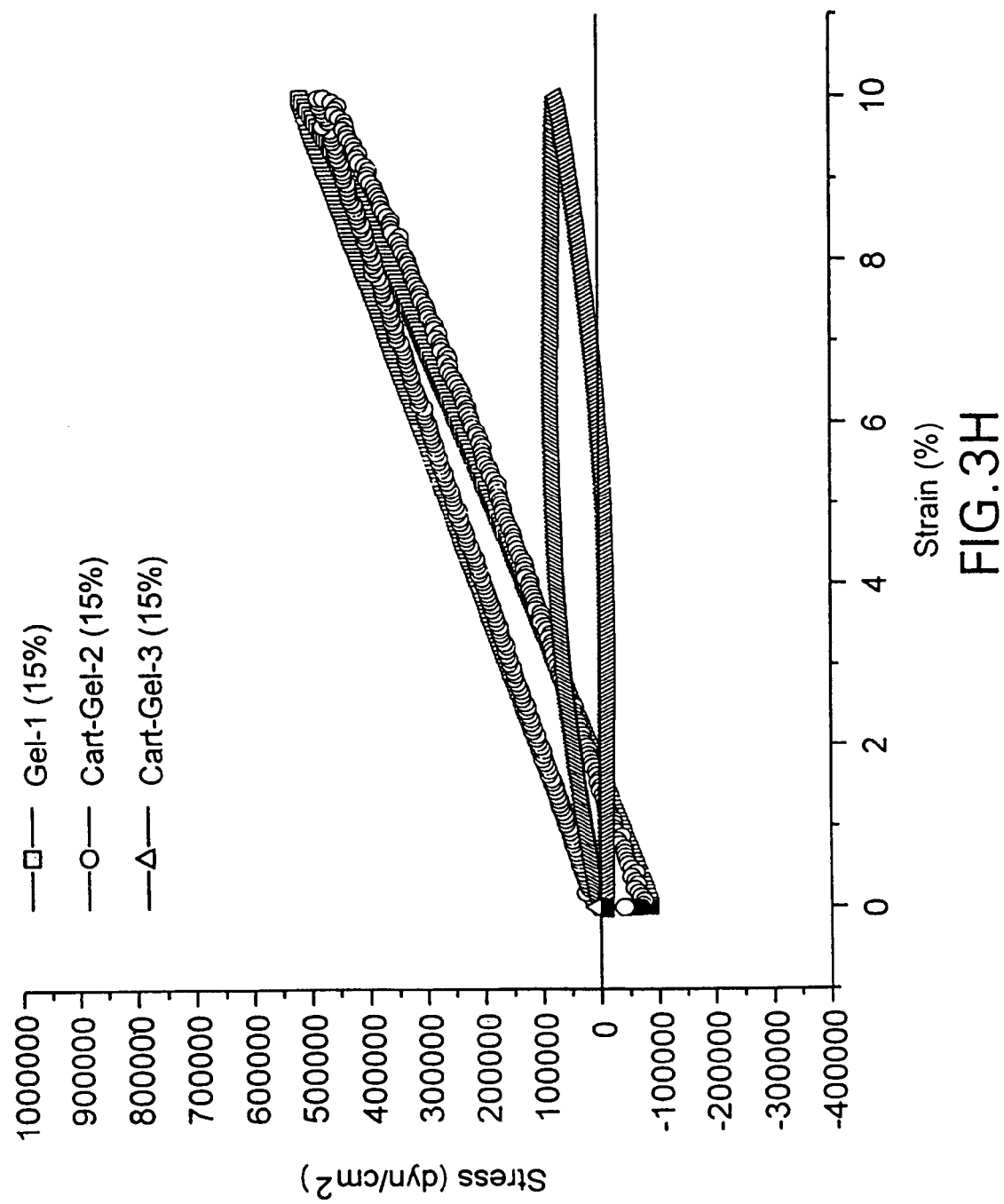
Figure 31:
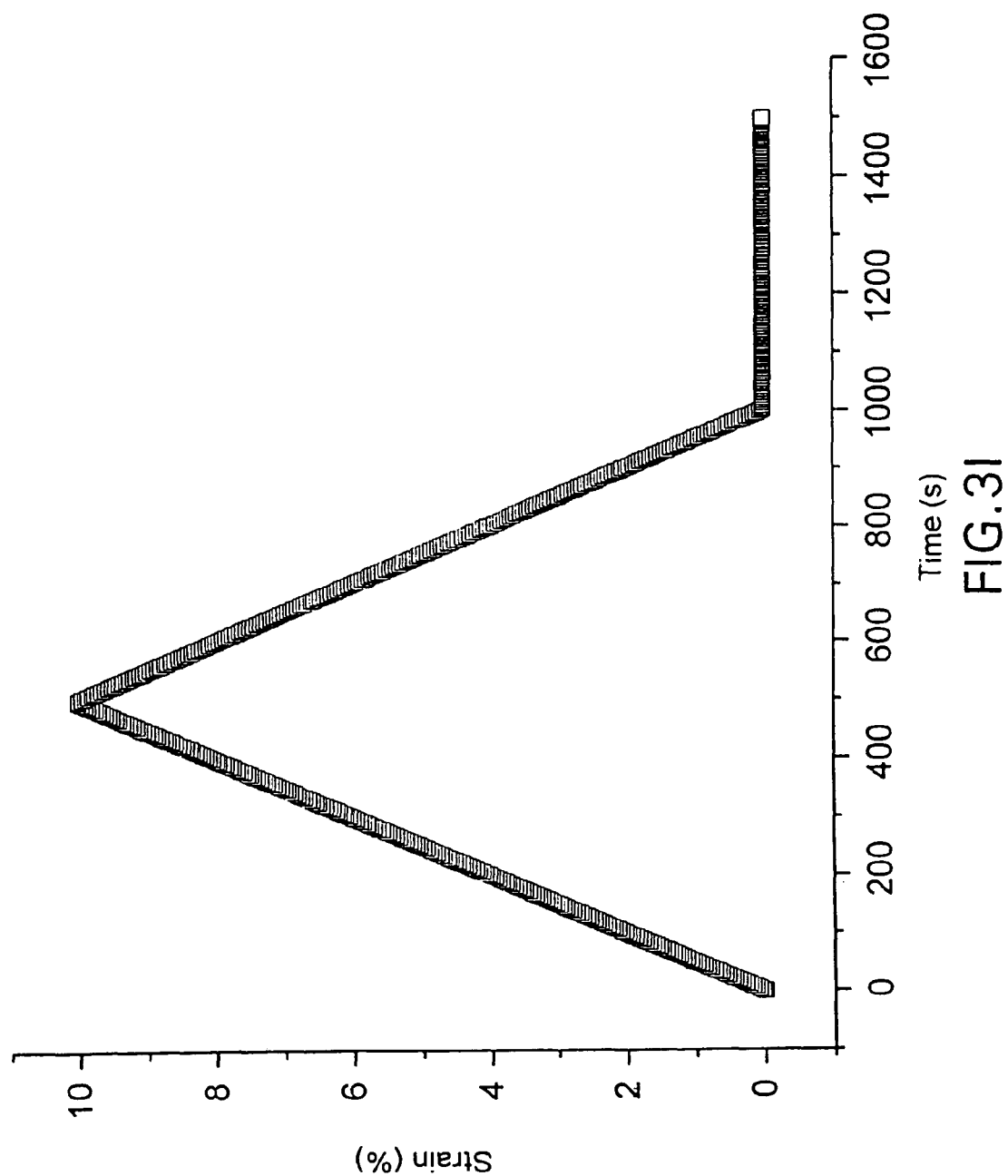

Chemical and morphological analysis was performed on the cartilage-biomaterial construct to confirm tissue-initiated polymerization and gel formation (FIG. 2). The superficial layer of native cartilage is a mixture of proteins, proteoglycans, and bonded water as seen chemically by Fourier transform infrared spectroscopy (ATR-FTIR) spectrum d. After enzymatic treatment of the cartilage surface with chondroitinase ABC, the poly(saccharide) peaks are diminished while the typical amide protein bands are further revealed FTIR spectrum c suggesting exposure of collagen on the cartilage surface. Hydrogels were synthesized on the cartilage surface using both tissue-initiated photopolymerization and a standard photoinitiating polymerization system. The cartilage surface at the interface was then analyzed following frozen fracture. Chemical and morphological analysis of the cartilage surface using the standard photoinitiating system showed little difference compared to the enzymatically-treated surface. However, chemical analysis of the cartilage surface subjected to tissue-initiated photopolymerization (spectrum a) demonstrates strong signals from the ether and ester carbonyl groups of the crosslinked network and the characteristic band of the poly(ethylene oxide) (PEO) macromer at 945 cm$^{-1}$ when compared to the standard photoinitiating polymerization system (spectrum b).

Directed covalent integration potentially provides a more stable biomaterial-tissue interface, therefore the mechanical functionality of the attachment was examined. After equilibration in phosphate-buffered saline for 24 hrs, the tissue-initiated cartilage-hydrogel complexes created using the tyrosyl-("CartGel"s) were cut into two pieces, as shown in FIG. 3. The upper half of the gel-layer was split off and named "Gel-1"; the same sized lower half of the gel together with its bond cartilage matrix (the complex) was named "Cart-Gel-2". PEODM gels (15% and 20%, w/v) were also made on the cartilage surfaces only treated with chondroitinase ABC (but without $H_2O_2$-treatment) by the initiation of 0.05% photoinitiator Irgacure® D-2959 (Ciba-Giegy) and named "Cart-Gel-3." The percentage of (radius/thickness)×radian×100% was recorded as the rotating torsion-strain. The rotation rate was programmed as 3.75×10$^{-4}$ rad/sec (strain: 0.02%/sec) for 500 sec, then reversing −3.75×10$^{-4}$ rad/sec for 500 sec, and finally maintaining 0-rate relaxation for 500 sec. The stress-strain-time profiles were automatically recorded by computer.

The results of the mechanical functionality testing are shown in FIG. 3. FIG. 3A is a schematic of the testing procedure. FIGS. 3B-D represent the stress-strain-time behavior of 15% gels and 20% gels. FIGS. 3 E-H represent the rheological behavior of "Gel-1" (squares), "Cart-Gel-2" (circles), and "Cart-Gel-3" (triangles). FIGS. 3E and 3G illustrates the stress over time of the samples. FIGS. 3F and 3H plot intersections of various stress and strain points of the diagram. FIG. 3I indicates the applied strain-time conditions.

Gel-1 exhibited standard viscoelastic behavior with high elasticity and eventual plastic distortion. The hydrogel-cartilage constructs, Cart-Gel-2, created by tissue-initiated polymerization exhibited similar viscoelastic behavior, with no evidence of slipping or failure. However, the hydrogel synthesized on the cartilage surface using a standard photoinitiating system, Cart-Gel-3, required little torsional stress to cause slipping on the cartilage surface. In contrast, the integrated gel is significantly attached to the tissue surface such that the gel will reach the limit of plastic deformation before slipping from the cartilage surface.

Example II

Analysis of the mechanism of the tissue-initiated polymerization and direct covalent integration according to the present invention was carried out in a simplified system using pure collagen protein and hydroxyethyl methacrylate (HEMA). Collagen was chosen as the target for reaction due to its universal presence and mechanical stability. Collagen contains tyrosine residues which may be oxidized to produce the initiating radical for polymerization. While tyrosine makes up only 0.6% of human Type II collagen, 90% of these residues are located at the protein C-terminus, providing a concentrated source of radicals for polymerization.

Type II collagen was reacted with $H_2O_2$ (1%) for 15 min. After the un-reacted $H_2O_2$ was removed, HEMA (250 mM) was added and the UV-irradiation (365 nm; 3 mW/cm$^2$) was performed for 5 min. The product solution was loaded into the Sephadex® (Amersham) G-25 size exclusion column to remove the excess HEMA monomer and the potential byproduct of oligo-HEMA. As a control, the reaction without $H_2O_2$-oxidation was also carried out. The purified products were lyophilized for ATR-FTIR analysis. All the solutions used in this experiment were pre-argon-bubbled.

Figure 4:
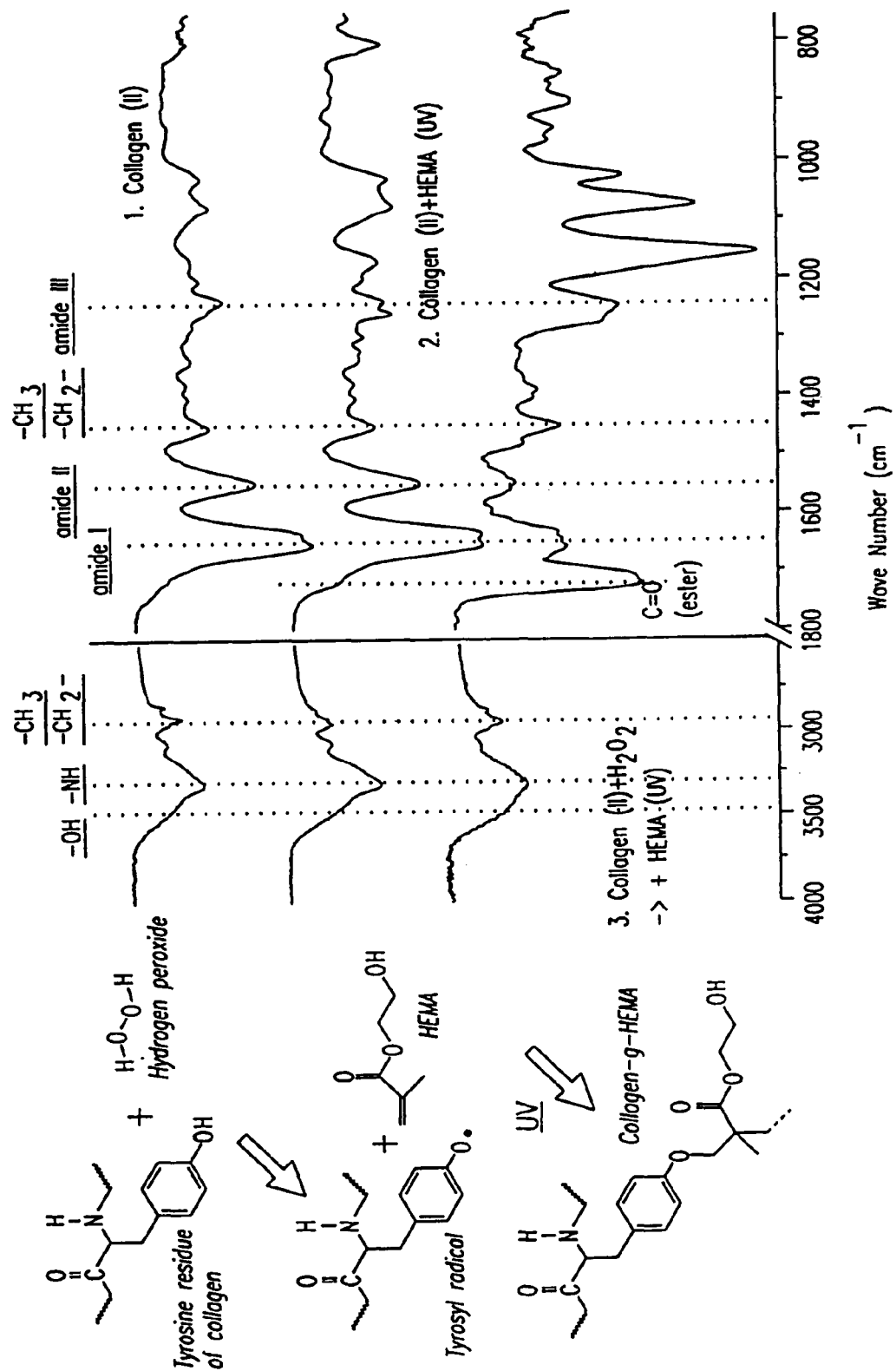
FIG. 4 shows the ATR-FTIR analysis illustrating formation of a covalent bond between collagen and hydroxyethyl methacrylate.

Conjugation of Type II collagen and HEMA was characterized by ATR-FTIR (FIG. 4). On the left the model reaction is shown, and on the right the ATR-FTIR spectra are shown. Type II collagen (Curve "1"), product of Type II collagen reacting with HEMA under UV-irradiation with (Curve "3") or without (Curve "2") pre-oxidation. The results indicate that with $H_2O_2$ oxidation and UV-irradiation, conjugation of collagen-HEMA is achieved with peaks from HEMA (ester carbonyl at 1718 cm$^{-1}$ and —C—O— peaks at 1150 cm$^{-1}$) and protein (amide peaks I, II, and III present at 1650 cm$^{-1}$, 1550 cm$^{-1}$, and 1245 cm$^{-1}$) present (Curve 3). Without oxidative treatment, photo-conjugation did not occur (Curve 2).

To confirm the mechanism of tissue-initiated polymerization an electron spin-trapping strategy was developed to isolate and confirm the protein-centered tyrosyl radical source for polymerization. Qian et al. demonstrated the ability of tyrosine residues on protein sequence to form tyrosyl radicals after mild oxidation (*Biochemical Journal*, vol. 363; pp. 281-288, (2002)).

MNP (2-methyl-2-nitrosopropane) was utilized as a spin trapping agent and probe for the tyrosyl radical using electron spin resonance (ESR). ESR profiles were recorded using a spectrometer operating 9.47 GHz with modulation of 100 KHz. All the solutions used in this experiment were pre-argon-bubbled. Bovine collagen (Type II, 2 mg/ml), MNP (100 mM) and $H_2O_2$ (0.5%) was mixed and allowed to react for 10 min. Similar mixtures without $H_2O_2$ or MNP were simultaneously prepared. The products were loaded into a Sephadex® (Amersham) G-25 size-exclusion column (SEC) to remove the excess $H_2O_2$, un-reacted MNP and non-protein spin adducts. A portion of the samples were directly characterized by ESR; the others were first non-specifically digested by pronase and then subjected to ESR in order to determine the site of radical adduct. Cartilage powders from the superficial layer were treated with chondroitinase ABC. Photo-oxidation was carried out by immersing the powders into 5% $H_2O_2$ in presence of MNP and exposing to the UV-irradiation (365 nm; 8 mW/cm$^2$) for 5 min. A portion of purified products was subjected to ESR; the others were digested by collagenase II/trypsin, and then subjected by ESR.

The results of the ESR spin-trapping are depicted schematically in FIG. 5. Schematic illustration of the MNP/tyrosyl ESR spin-trapping are on the left and ESR spectra are on the right. The combination of tyrsine, MNP, horseradish peroxidase (HRP), and $H_2O_2$ produced an ESR spectrum with a characteristic hyperfine coupling ($\alpha^N$) of the tyrosyl radical, 15.5 G (spectrum g). A broad ESR line (>10 G) with a large molecular rotational correlation time, $\tau_c$, is detected when collagen is treated with $H_2O_2$ and MNP (spectrum c), indicating that the MNP trapping is located on a macromolecule. After digestion with pronase (spectrum d), the ESR lines are clarified and demonstrate an $\alpha^N$ of 15.5 G as in spectrum a with the pure tyrosyl radical. A similar phenomenon is observed when cartilage tissue is treated with MNP and an oxidative agent (spectrum e), and subsequent enzymatic digestion (with Type II Collagenase and trypsin, spectrum f). The resulting ESR curve is equivalent to the characteristic tyrosyl radical presented in spectrum a (Type II collagen and $H_2O_2$, without MNP). The conditions of Type II collagen and MNP, without $H_2O_2$-oxidation are shown in spectrum b. Radicals were not detected in control curves from collagen treated without $H_2O_2$ or without the MNP radical trapper. The ESR data in this simplified model system confirmed the hypothesized production of a tyrosyl radical on collagen in cartilage after a mild oxidative reaction.

Compatibility of directed covalent attachment is critical for preventing host tissue damage and for applications where delivery and encapsulation of cells in the biomaterial is desired. The biocompatibility of the treatment procedure and directed biomaterial tissue attachment was investigated by determining viability of cells in situ in the tissue and of cells encapsulated in the attached biomaterial. The compatibility of the tissue enzyme and oxidative treatment was investigated first using a fluorescent live-dead cell assay. We have been aware that enzymatic treatment of cartilage does not affect cell viability while merely cutting the tissue causes adjacent cell death.

Figure 6:
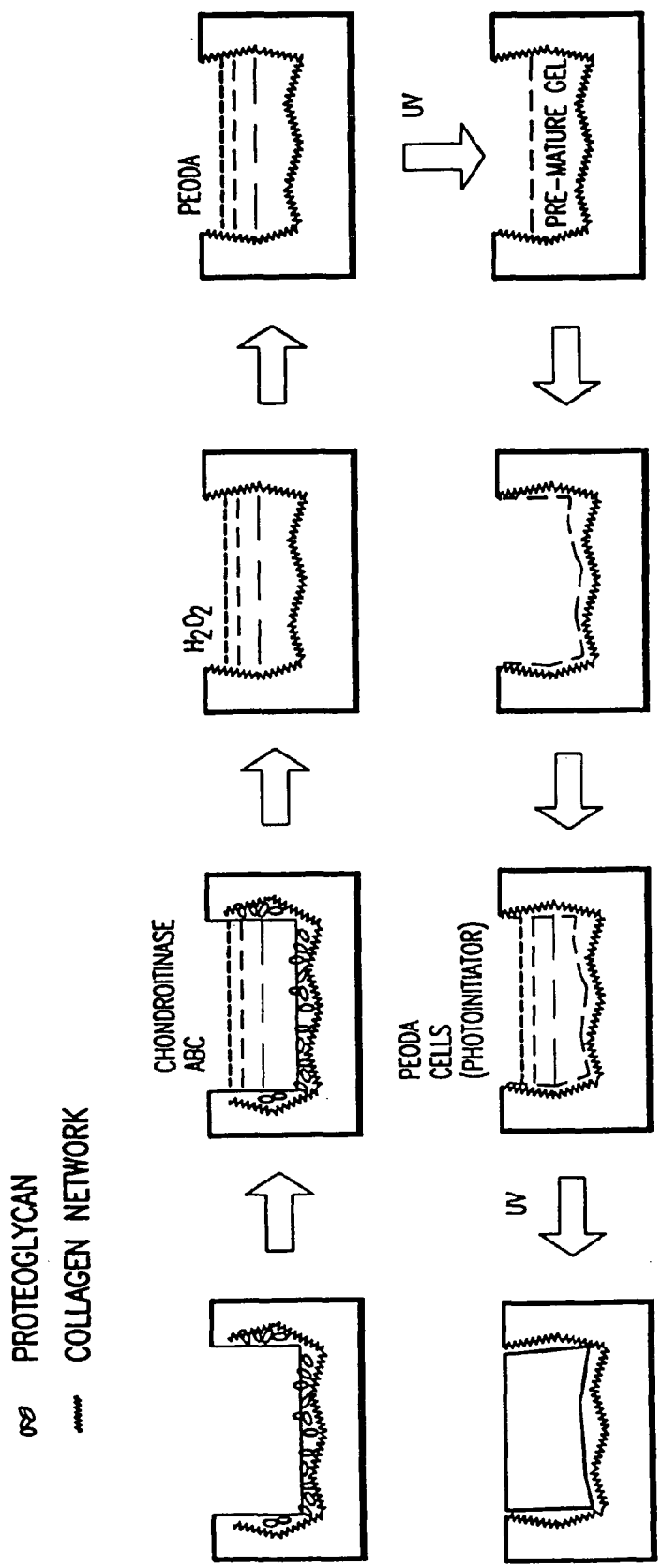
FIG. 6 illustrates the procedure for measuring biocompatibility of L the process.

Following the chondroitinase ABC enzymolysis on the defect surface of a fresh fetal bovine cartilage for 1 hr (37° C.), the photo-oxidation was performed respectively with 2%, 5% and 10% $H_2O_2$ under UV-irradiation (365 nm; 3 mW/cm$^2$; 5 min). After clearance of excess $H_2O_2$, pre-argon-bubbled PEODM solutions (15%, w/v) were added into the cartilage defect without photo-initiators. The photo-grafting reaction was allowed to proceed for 10 min (365 nm UV, 8 mW/cm$^2$). Then the sticky liquid-like premature gel was sucked off and replaced by the mixture of macromer (15% PEODM) together with 2 million/ml Passage 4 bovine chondrocytes and 0.05% (w/w) photo-initiator D-2959 in PBS (pH 7.4). The photopolymerization/cell-encapsulation was carried out under UV-irradiation (365 nm, 3 mW/cm$^2$) for 5 min. The method is illustrated schematically in FIG. 6. The cartilage or cartilage-hydrogel slices from each step described above were prepared for the qualitative cytotoxicity evaluation by Live/Dead assay (Molecular Probes, Inc., Eugene, Oreg.). The biocompatibility of the enzymatic treatment for covalent integration confirmed that no additional cell death is observed. A dose-response effect of cell death was observed with oxidative treatment, such that increasing cell death was observed with increasing $H_2O_2$ concentration. The $H_2O_2$ concentration of 2% allows tissue-initiated photopolymerization and integration to proceed in a biocompatible manner, without excessive cell death.

EXAMPLES AND TESTING OF
ALDEHYDE-MEDIATED INTEGRATION

The below examples illustrate the method according to the present invention.

Example III

Figure 7:
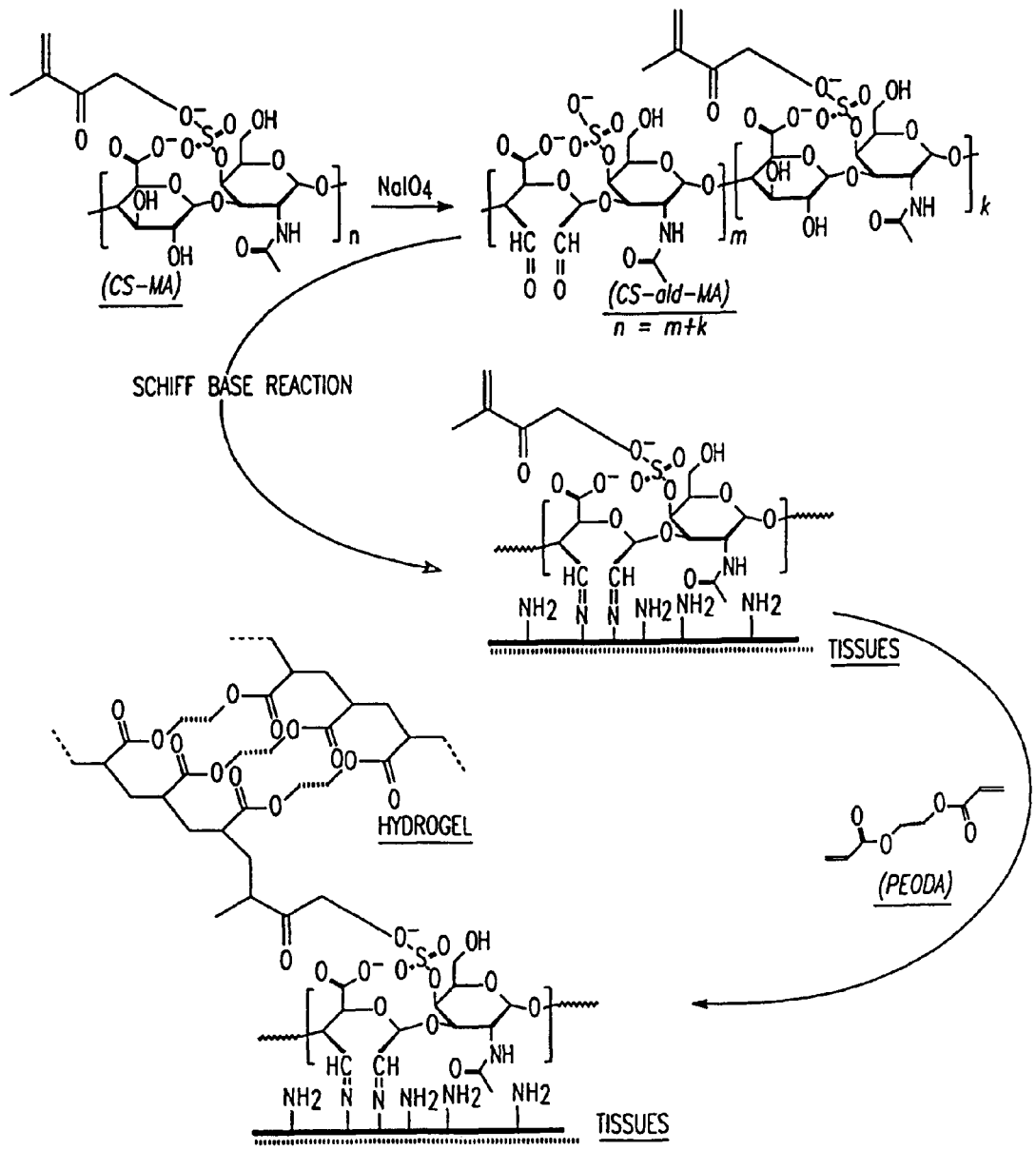
FIG. 7 shows an example of the aldehyde priming embodiment of the invention.

FIG. 7 illustrates the aldehyde priming embodiment of the invention. The method described below may be found in more detail in Li et al., *Macromolecules* vol. 36, pp. 2556-2562 (2003), the entire disclosure of which is hereby incorporated by reference.

Chondroitin sulfate A sodium salt (CS, 10 g, ~20 mmol disaccharide repeating unit) was dissolved in 100 ml phosphate buffer saline (PBS, pH 7.4), followed by addition of glycidyl methacrylate (GMA, 3 g, ~20 mmol) while vigorously stirring at room temperature for 1 to 15 days. The purification was performed by anhydrous acetone extraction twice to remove all the compounds that failed to covalently graft onto CS chains. The purified products were lyophilized for 48 hrs. The final yield of chondroitin sulfate methacrylate (CS-MA) product was all 7 to 8 g.

Six hundred mg of CS-MA (0.8~1.2 mmol of adjacent diol, 70% CS-A, Sigma) and 616 mg of sodium periodate (~2.88 mmol, $NaIO_4$, Sigma) were dissolved together in 10 ml of de-ionized water and protected from light. The reaction was allowed to continue for ~14 hr in dark with vigorous stirring. The insoluble byproducts were removed with a 0.22 μm filter and the product was loaded into a Sephadex® G-25 size exclusion chromatography (SEC) column, by which the product was purified from the water-soluble byproducts and unreacted small molecules. The product, chondroitin sulfate-aldehyde-methacrylate (CS-ald-MA), was obtained by lyophilization, with a yield of ~90%. The determination of aldehyde substitution degree was performed via a hydroxylamine hydrochloride titration. The result was 60 to 70%. The tissue adhesive was formulated by mixing equal volumes (20 μl) of 25% CS-ald and 40% bovine serum albumin (BSA, Sigma). The adhesive was used immediately after the formulation and the reaction was completed in 2 to 5 min with the Schiff-base mechanism.

The resulting compound provides a chondroitin with both aldehyde and methacrylate groups to integrate a surface of an extracellular matrix with a photopolymerizing polymer, thereby serving as a priming agent, as illustrated in FIG. 7.

EXAMPLES AND TESTING OF ANIMAL MODELS

Example IV

In a further in vitro illustrative of the method according to the present invention, chondral (n=4) and osteochondral (n=4) defects were created on the medial and lateral tibial surface of bovine knees obtained from an abattoir. Chondral and osteochondral defects (d=1 cm) were created using a curette and drill at a depth of approximately 2 and 5 mm, respectively. Saline was injected into the joint and surrounding tissue to maintain hydration in the cadaveric leg during simulation. A 1 lb. weight was placed on the leg to further simulate natural forces and movement.

A hydrogel implant was applied. The hydrogel solution was prepared by thoroughly mixing 10% w/v of poly(ethylene) oxide diacrylate (Shearwater, PEODA) and the photoinitiator, Irgacure® 2959 (Ciba, 0.05% w/v final concentration), in sterile PBS with 100 U/ml of penicillin and 100 ug/ml streptomycin (Gibco). TGF-β3 (RDI, 150 ng/ml) was added to the hydrogel solutions.

All hydrogel implants remained in the chondral defects after exposure to overnight mechanical stress (n=4). No hydrogel debris was observed in the joint space. Fifty percent of the hydrogels in the osteochondral defects remained in place after simulation. The hydrogels in the larger osteochondral defects appeared to swell, causing them to protrude from the defects. Thus, chondral defects were used as a model to examine cartilage regeneration in the goat.

Example V

Mesenchymal stem cells (MSCs) were isolated from femoral aspirates of 3 to 3½ year old goats and expanded in Mesenchymal Stem Cell Medium (Clonetics, MSCGM). Passage 3 cells were trypsinized, washed in serum free medium, and then resuspended in the hydrogel solution immediately prior to implantation.

The hydrogel solution was prepared by thoroughly mixing 10% w/v of poly(ethylene) oxide diacrylate (Shearwater, PEODA) and the photoinitiator, Irgacure 2959 (Ciba, 0.05% w/v final concentration), in sterile PBS with 100 U/ml of penicillin and 100 ug/ml streptomycin (Gibco). TGF-β3 (RDI, 150 ng/ml) was added to the hydrogel solutions and MSCs were resuspended in the polymer solution at a concentration of 20 million cells/ml and gently mixed to make a homogeneous suspension.

Two defects were created on the medial tibial plateau and one on the lateral femoral condyle on hind limb of two goats (2-3 years old) using a curette. Defects were critical-size (5 mm diameter) such that natural repair would not occur. Experimental defects (n=4) were filled with polymer, MSCs (allogeneic), hyaluronic acid (to enhance viscosity) and TGF-β3. The cell-polymer suspension was added and polymerized until the defect was completely filled. The samples were photo-polymerized with a 5 minute exposure to long-wave, 365 nm UV light at 4 mW/cm$^2$ (Acticure). Control defects included an empty defect and a defect containing only polymer (n=2). After wound closure, the legs were cast for two weeks after which the animals were allowed to move ad lib. Samples were harvested for gross and histological observation after 2 and 4 weeks of implantation.

After casts were removed at two weeks post implantation, no swelling or infection was observed. Before harvesting at one month, the goat demonstrated active movement without any limb favoring or lameness. Samples harvested after two weeks grossly showed minimal evidence of regeneration. However, samples harvested one month after implantation demonstrated significant evidence of regeneration. The experimental defect where the photopolymerizing MSC-hydrogel construct was placed showed significantly more cartilage tissue in the defect space compared to the control defect which did not contain a gel. The femoral defects also contained repair tissue after one month.

This study demonstrates the application of a photopolymerizing hydrogel system for cartilage repair according to the present invention in a large animal model. Cartilage has been generated from goat MSCs photoencapsulated in a hydrogel and incubated in vitro. The photopolymerizing hydrogel system has been applied in vivo in mice and rats but has not been introduced into a joint environment. Recently allogenic MSCs have been successfully applied in cardiac repair systems suggesting their possible use for cartilage repair. Allogeneic MSCs are an ideal cell source since no additional surgical procedure is required to obtain cells before hydrogel treatment. This in vivo work did not specifically use any integration method but is an example of when we would use it.

While the present invention has been described with reference to certain preferred embodiments, one of ordinary skill in the art will recognize that additions, deletions, substitutions, modifications and improvements can be made while remaining within the spirit and scope of the present invention as defined by the appended claims.

Although cartilage was used as a model tissue in examples I and II, the embodiments pertaining to those examples will function in other tissues containing tyrosine residues, the tyrosine residues being disposed in either collagen or another protein of the extracellular matrix. Likewise, while $H_2O_2$ was used as an oxidizer in examples I and II, other oxidizing agents may be used, for example vitamin C. Although Example I used poly(ethylene glycol) dimethacrylate (PEODM) and Example II used hydroxyethyl methacrylate (HEMA), any polymerizable agent with an acrylate may be used in those embodiments, as herein disclosed.

Although Example III used albumin as a carrier, other agents can be used besides albumin. For example, polyethlyimine (PEI) or another agent containing amino groups may be used. Further regarding Example III, although chondroitin sulfate was modified to produce an agent with aldehyde and methacrylate groups, other saccharides may also be used. Still further regarding example III, although the priming agent contained a methacrylate group for binding to the polymerizable agent, other chemical groups may be used instead.

Although Examples IV and V used photoinitiators, the tyrosyl-acrylate or aldehyde embodiments described herein may be used. Moreover, use of the invention in living tissue is not limited to the exact compositions described in the examples.

Although ultraviolet (UV) light is used in various instances throughout the examples, visible light or other forms of electromagnetic radiation may also be used to achieve the same purposes depending on the chemistry involved.

What is claimed is:

1. A method of integrating a hydrogel to the extracellular matrix of a bone, comprising the steps of:
   (a) priming the surface of a bone by treating the bone with a priming agent to create a primed bone, wherein the priming agent comprises a polysaccharide with at least one produced aldehyde group and a first at least one free radical polymerizable group wherein the aldehyde is produced by treating said polysaccharide with periodate, and the least one produced aldehyde group reacts with the extracellular matrix of the bone to covalently bind the extracellular matrix of the bone and the priming agent;
   (b) adding to the primed bone a polymerizable agent, wherein the polymerizable agent comprises a second at least one free radical polymerizable group; and
   (c) reacting the primed bone and the polymerizable agent by a radical reaction to create a hydrogel covalently bound to the bone; wherein the radical reaction is between the first and second free radical polymerizable groups, and the first and second free radical polymerizable groups are each independently selected from the group consisting of an acrylate, diacrylate, oligoacrylate, methacrylate, dimethacrylate, and oligo methacrylate.

2. The method of claim 1, wherein said bone is disposed in a mammal.

3. The method of claim 1, wherein the polysaccharide is chondroitin sulfate.

4. The method of claim 1, wherein said reacting step further comprises exposing said primed bone and said polymerizable agent to ultraviolet radiation.

5. The method of claim 1, wherein the polymerizable agent comprises biologically active material.

6. The method of claim 5, wherein the biologically active material comprises autologous cells.

7. The method of claim 5, wherein the biologically active material comprises a growth factor.

8. A hydrogel produced by a method comprising:
   (a) priming the surface of a bone by treating the bone with a priming agent comprising a polysaccharide with at least one produced aldehyde group and a first at least one free radical polymerizable group wherein the aldehyde is produced by treating said polysaccharide with periodate, to create a primed bone, wherein the least one produced aldehyde group reacts with the extracellular matrix of the bone to covalently bind the extracellular matrix of the bone and the priming agent;
   (b) adding to the primed bone a polymerizable agent, wherein the polymerizable agent comprises a second at least one free radical polymerizable group; and
   (c) reacting the primed bone and the polymerizable agent by a radical reaction to create a hydrogel covalently bound to the bone; wherein the radical reaction is between the first and second free radical polymerizable groups, and the first and second free radical polymerizable groups are each independently selected from the group consisting of an acrylate, diacrylate, oligoacrylate, methacrylate, dimethacrylate, and oligo methacrylate.

9. The hydrogel of claim 8, wherein said bone is disposed in a mammal.

10. The hydrogel of claim 8, wherein the polysaccharide is chondroitin sulfate.

11. The hydrogel of claim 8, wherein said reacting further comprises exposing said primed bone and said polymerizable agent to ultraviolet radiation.

12. The hydrogel of claim 8, wherein the polymerizable agent comprises biologically active material.

13. The hydrogel of claim 12, wherein the biologically active material comprises autologous cells.

14. The hydrogel of claim 12, wherein the biologically active material comprises a growth factor.

15. A method of integrating a hydrogel to the extracellular matrix of an osteochondral defect, comprising the steps of:
   (a) priming the surface of an osteochondral defect by treating the osteochondral defect with a priming agent to create a primed osteochondral defect, wherein the priming agent comprises a polysaccharide with at least one produced aldehyde group and a first at least one free radical polymerizable group wherein the aldehyde is produced by treating said polysaccharide with periodate, and the least one produced aldehyde group reacts with the extracellular matrix of the osteochondral defect to covalently bind the extracellular matrix of the osteochondral defect and the priming agent;
   (b) adding to the primed osteochondral defect a polymerizable agent, wherein the polymerizable agent comprises a second at least one free radical polymerizable group; and
   (c) reacting the primed osteochondral defect and the polymerizable agent by a radical reaction to create a hydrogel covalently bound to the osteochondral defect; wherein the radical reaction is between the first and second free radical polymerizable groups, and the first and second free radical polymerizable groups are each independently selected from the group consisting of an acrylate, diacrylate, oligoacrylate, methacrylate, dimethacrylate, and oligo methacrylate.

16. The method of claim 15, wherein said osteochondral defect is disposed in a mammal.

17. The method of claim 15, wherein the polysaccharide is chondroitin sulfate.

18. The method of claim 15, wherein said reacting step further comprises exposing said primed osteochondral defect and said polymerizable agent to ultraviolet radiation.

19. The method of claim 15, wherein the polymerizable agent comprises biologically active material.

20. The method of claim 19, wherein the biologically active material comprises autologous cells.

21. The method of claim 19, wherein the biologically active material comprises a growth factor.

22. A hydrogel produced by a method comprising:

(a) priming the surface of an osteochondral defect by treating the osteochondral defect with a priming agent comprising a polysaccharide with at least one produced aldehyde group and a first at least one free radical polymerizable group wherein the aldehyde is produced by treating said polysaccharide with periodate, to create a primed osteochondral defect, wherein the least one produced aldehyde group reacts with the extracellular matrix of the osteochondral defect to covalently bind the extracellular matrix of the osteochondral defect and the priming agent;

(b) adding to the primed osteochondral defect a polymerizable agent, wherein the polymerizable agent comprises a second at least one free radical polymerizable group; and (c) reacting the primed osteochondral defect and the polymerizable agent by a radical reaction to create a hydrogel covalently bound to the osteochondral defect; wherein the radical reaction is between the first and second free radical polymerizable groups, and the first and second free radical polymerizable groups are each independently selected from the group consisting of an acrylate, diacrylate, oligoacrylate, methacrylate, dimethacrylate, and oligo methacrylate.

23. The hydrogel of claim 22, wherein said osteochondral defect is disposed in a mammal.

24. The hydrogel of claim 22, wherein the polysaccharide is chondroitin sulfate.

25. The hydrogel of claim 22, wherein said reacting further comprises exposing said primed osteochondral defect and said polymerizable agent to ultraviolet radiation.

26. The hydrogel of claim 22, wherein the polymerizable agent comprises biologically active material.

27. The hydrogel of claim 26, wherein the biologically active material comprises autologous cells.

28. The hydrogel of claim 26, wherein the biologically active material comprises a growth factor.

* * * * *